US010112949B2

(12) United States Patent
Andrés-Gil et al.

(10) Patent No.: US 10,112,949 B2
(45) Date of Patent: Oct. 30, 2018

(54) 6,7-DIHYDROPYRAZOLO[1,5-A]PYRAZIN-4(5H)-ONE COMPOUNDS AND THEIR USE AS NEGATIVE ALLOSTERIC MODULATORS OF MGLUR2 RECEPTORS

(71) Applicant: Janssen Pharmaceutica NV, Beerse (BE)

(72) Inventors: José Ignacio Andrés-Gil, Madrid (ES); Michiel Luc Maria Van Gool, Madrid (ES); Andrés Avelino Trabanco-Suárez, Olias del Rey (ES); Ana Isabel De Lucas Olivares, Bargas (ES); Sergio Alvar Alonso-de Diego, Toledo (ES); Óscar Delgado-González, Santa Cruz de Tenerife (ES)

(73) Assignee: Janssen Pharmaceutica NV, Beerse (BE)

( * ) Notice: Subject to any disclaimer, the term of this patent is extended or adjusted under 35 U.S.C. 154(b) by 59 days.

(21) Appl. No.: 15/500,553

(22) PCT Filed: Jul. 30, 2015

(86) PCT No.: PCT/EP2015/067533
§ 371 (c)(1),
(2) Date: Jan. 31, 2017

(87) PCT Pub. No.: WO2016/016381
PCT Pub. Date: Feb. 4, 2016

(65) Prior Publication Data
US 2018/0222908 A1  Aug. 9, 2018

(30) Foreign Application Priority Data

Aug. 1, 2014  (EP) .................................... 14179599

(51) Int. Cl.
*A61P 25/26* (2006.01)
*A61P 25/18* (2006.01)
*C07D 487/04* (2006.01)

(52) U.S. Cl.
CPC ............ *C07D 487/04* (2013.01); *A61P 25/18* (2018.01); *A61P 25/26* (2018.01)

(58) Field of Classification Search
None
See application file for complete search history.

(56) References Cited

FOREIGN PATENT DOCUMENTS

| EP | 2666775 A1 | 11/2013 |
|---|---|---|
| WO | 2010130424 B9 | 11/2010 |
| WO | 2012083224 A1 | 6/2012 |
| WO | 2013066736 A1 | 5/2013 |
| WO | 2013174822 A1 | 11/2013 |
| WO | 2013192343 A1 | 12/2013 |
| WO | 2013192347 A1 | 12/2013 |
| WO | 2013192350 A1 | 12/2013 |
| WO | 2014064028 A1 | 5/2014 |

OTHER PUBLICATIONS

Alfonso R Gennaro, 18th edition Remington's—Pharmaceutical Sciences, 18th edition Remington's—Pharmaceutical Sciences, 1990, Part 8_ Pharmaceutical preparations and their Manufacture_ pp. 1435-1714, Part 8.
Alper R. et al, Agonist-Stimulated [35S]GTBgS Binding, Current Protocols in Pharmacology, 1998, suppl.2.
Celia Goeldner, Cognitive impairment in major depression and the mGlu2 receptor as a therapeutic target, Neuropharmacology, Aug. 3, 2013, pp. 337-346, 64.
CID Jose Maria et al, Discovery of 3-Cyclopropylmethyl-7-(4-phenylpiperidin-1-yl)-8-trifluoromethyl[1,2,4]triazolo [4,3-a]pyridine (JNJ-42153605): A Positive Allosteric Modulator of the Metabotrophic Glutamate 2 Receptor, Journal of Medicinal Chemistry, Oct. 16, 2012, pp. 8770-8789, 55.
Embrechts S. et al, Longitudinal characterisation of the TauPS2APP mouse model of Alzheimer's disease in a two trial discrimination task of visuo-spatial recognition memory, 45th European Brain and Behaviour Society Meeting Sep. 6-9, 2013 Munich, Sep. 6, 2009, p. 202, not applicable.
Ferraguti,et al, Metabotropic glutamate receptors, Cell & Tissue Research, Jul. 18, 2006. pp. 483-504, 326.
Hiroyuki Koike et al, Role of BDNF/TrkB Signaling in antidepressant-like effects of a group II metabotropic glutamate receptor antagonist in animal models of depression, Behavioural Brain Research, Oct. 23, 2012, pp. 48-52, 238.
Kelmendi et al, The Role of the Glutamatergic system in the pathophysiology and treatment of mood disorders, Primary Psychiatry, Oct. 2006, pp. 80-86, vol. 13 No. 10.
Li Jingjie et al, Palladium-Catalyzed Oxidative Rearrangement of Tertiary Allylic Alcohols to Enones with Oxygen in Aqueous Solvent, Organic Letters, Oct. 3, 2014, pp. 5370-5373, No. 16.
NCT01457677, View of NCT01457677 on Feb. 18, 2014, ClinicalTrials.gov Archive, Feb. 18, 2014, pp. 1-3, not applicable.
Niswender Colleen M. et al, Metabotropic Glutamate Receptors: Physiology, Pharmacology, and Disease, Annu.Rev.Pharmacol.Toxicol., 2010, pp. 295-322, 50.
Schaffhauser et al, Pharmacological Characterization and Identification of Amino Acids Involved in the Positive Modulation of Metabotropic Glutamate Receptor Subtype 2, Molecular Pharmacology, Jun. 13, 2003, pp. 798-810, vol. 64, No. 4.
International Search Report for PCT/EP2015/067530 dated Nov. 2, 2015.

(Continued)

*Primary Examiner* — Samantha L Shterengarts

(57) ABSTRACT

The present invention relates to novel 6,7-dihydropyrazolo [1,5-a]pyrazin-4(5H)-one derivatives as negative allosteric modulators (NAMs) of the metabotropic glutamate receptor subtype 2 ("mGluR2"). The invention is also directed to pharmaceutical compositions comprising such compounds, to processes for preparing such compounds and compositions, and to the use of such compounds and compositions for the prevention or treatment of disorders in which the mGluR2 subtype of metabotropic receptors is involved.

24 Claims, No Drawings

(56) References Cited

OTHER PUBLICATIONS

International Search Report for PCT/EP2015/067572 dated Sep. 9, 2015.
International Search Report for PCT/EP2015/067534 dated Sep. 10, 2015.
International Search Report for PCT/EP2015/067538 dated Sep. 9, 2015.

6,7-DIHYDROPYRAZOLO[1,5-A]PYRAZIN-4(5H)-ONE COMPOUNDS AND THEIR USE AS NEGATIVE ALLOSTERIC MODULATORS OF MGLUR2 RECEPTORS

CROSS REFERENCE TO RELATED APPLICATIONS

This application is the national stage of PCT Application No. PCT/EP2015/067533, filed Jul. 30, 2015, which claims priority from European Patent Application No. 14179599.7, filed Aug. 1, 2014 the entire disclosures of which are hereby incorporated in their entirety.

FIELD OF THE INVENTION

The present invention relates to novel 6,7-dihydropyrazolo[1,5-a]pyrazin-4(5H)-one derivatives as negative allosteric modulators (NAMs) of the metabotropic glutamate receptor subtype 2 ("mGluR2"). The invention is also directed to pharmaceutical compositions comprising such compounds, to processes for preparing such compounds and compositions, and to the use of such compounds and compositions for the prevention or treatment of disorders in which the mGluR2 subtype of metabotropic receptors is involved.

BACKGROUND OF THE INVENTION

The glutamatergic system in the CNS is one of the neurotransmitter systems that play a key role in several brain functions. Metabotropic glutamate receptors (mGluR) belong to the G-protein-coupled family, and eight different subtypes have been identified to date, which are distributed to various brain regions (Ferraguti & Shigemoto, Cell & Tissue Research, 326:483-504, 2006). mGluRs participate in the modulation of synaptic transmission and neuronal excitability in the CNS by the binding of glutamate. This activates the receptor to engage intracellular signaling partners, leading to cellular events (Niswender & Conn, Annual Review of Pharmacology & Toxicology 50:295-322, 2010).

mGluRs are further divided into three subgroups based on their pharmacological and structural properties: group-I (mGluR1 and mGluR5), group-II (mGluR2 and mGluR3) and group-III (mGluR4, mGluR6, mGluR7 and mGluR8). Group-II ligands, both orthosteric and allosteric modulating, are considered to be potentially useful in the treatment of various neurological disorders, including psychosis, mood disorders, Alzheimer disease and cognitive or memory deficiencies. This is consistent with their primary localisation in brain areas such as the cortex, hippocampus and the striatum (Ferraguti & Shigemoto, Cell & Tissue Research 326:483-504, 2006). Particularly antagonists and negative allosteric modulators are reported to hold potential for the treatment of mood disorders and cognitive or memory dysfunction. This is based on findings with group-II receptor antagonists and negative allosteric modulators tested in laboratory animals subjected to a range of experimental conditions deemed relevant to these clinical syndromes (Goeldner et al, Neuropharmacology 64:337-346, 2013). Clinical trials are, for example, underway with mGluR2/3 antagonist decoglurant RO4995819 (F. Hoffmann-La Roche Ltd.) in adjunctive therapy in patients with Major Depressive Disorder having inadequate response to ongoing antidepressant treatment (ClinicalTrials.gov Identifier NCT01457677, retrieved 19 Feb. 2014).

WO 2013066736 (Merck Sharp & Dohme Corp.) describes quinoline carboxamide and quinoline carbonitrile compounds as mGluR2 NAMs. WO2013174822 (Domain Therapeutics) describes 4H-pyrazolo[1,5-a]quinazolin-5-ones and 4H-pyrrolo-[1,2-a]quinazolin-5-ones and in vitro mGluR2 NAM activity thereof. WO 2014064028 (F. Hoffman-La Roche AG) discloses a selection of mGlu2/3 negative allosteric modulators and their potential use in the treatment of Autistic Spectrum Disorders (ASD).

The group-II receptors are mainly located on presynaptic nerve terminals where they exert a negative feedback loop to the release of glutamate into the synapse (Kelmendi et al, Primary Psychiatry 13:80-86, 2006). Functional inhibition of these receptors by antagonists or negative allosteric modulators therefore lifts the brake on glutamate release, resulting in enhanced glutamatergic signaling. This effect is believed to underlie the antidepressant-like and procognitive effects observed in preclinical species with inhibitors of the Group-II receptor. In addition, treatment of mice with group-II orthosteric antagonists has been shown to enhance signaling by growth factors such as brain derived neurotrophic factor (BDNF) (Koike et al, Behavioural Brain Research 238:48-52, 2013). Since BDNF and other growth factors have been shown to be critically involved in mediating synaptic plasticity, this mechanism is likely to contribute to both antidepressant and procognitive properties of these compounds. Inhibition of mGluRs of the group-II receptor family is therefore considered to represent a potential therapeutic mechanism for neurological disorders, including depression and cognitive or memory dysfunction.

DESCRIPTION OF THE INVENTION

The present invention is directed to 6,7-dihydropyrazolo[1,5-a]pyrazin-4(5H)-one derivatives of Formula (I)

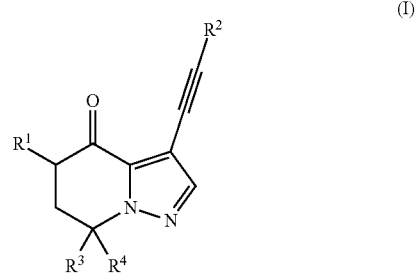

and stereoisomeric forms thereof, wherein
$R^1$ is phenyl or 2-pyridinyl, each optionally substituted with one or more substituents each independently selected from the group consisting of halo, $C_{1-4}$alkyl, monohalo-$C_{1-4}$alkyl, polyhalo-$C_{1-4}$alkyl, —$C_{1-4}$alkyl-OH, —CN, —$C_{1-4}$alkyl-O—$C_{1-4}$alkyl, $C_{3-7}$cycloalkyl, —O—$C_{1-4}$alkyl, monohalo-$C_{1-4}$alkyloxy, polyhalo-$C_{1-4}$alkyloxy, $SF_5$, $C_{1-4}$alkylthio, monohalo-$C_{1-4}$alkylthio and polyhalo-$C_{1-4}$alkylthio;
$R^2$ is selected from the group consisting of phenyl and pyridinyl, each of which is optionally substituted with one or more substituents each independently selected from the group consisting of halo, $C_{1-4}$alkyl, monohalo-$C_{1-4}$alkyl, polyhalo-$C_{1-4}$alkyl, —OH, —O—$C_{1-4}$alkyl, —$C_{1-4}$alkyl-O—$C_{1-4}$alkyl, monohalo-$C_{1-4}$alkyloxy, polyhalo-$C_{1-4}$alkyloxy, —$C_{1-4}$alkyl-OH, and $NR^{5a}R^{5b}$;
wherein $R^{5a}$ and $R^{5b}$ are each independently selected from hydrogen and $C_{1-4}$alkyl;

$R^3$ is selected from hydrogen and $C_{1-4}$alkyl;
$R^4$ is selected from the group consisting of hydrogen, $C_{1-4}$alkyl, monohalo-$C_{1-4}$alkyl, polyhalo-$C_{1-4}$alkyl, —$C_{1-4}$alkyl-O—$C_{1-4}$alkyl, and —$C_{1-4}$alkyl-OH;
and the N-oxides, and the pharmaceutically acceptable salts and the solvates thereof.

The present invention also relates to a pharmaceutical composition comprising a therapeutically effective amount of a compound of Formula (I) and a pharmaceutically acceptable carrier or excipient.

Additionally, the invention relates to a compound of Formula (I) for use as a medicament, and to a compound of Formula (I) for use in the treatment or in the prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

The invention also relates to the use of a compound of Formula (I) in combination with an additional pharmaceutical agent for use in the treatment or prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

Furthermore, the invention relates to a process for preparing a pharmaceutical composition according to the invention, characterized in that a pharmaceutically acceptable carrier is intimately mixed with a therapeutically effective amount of a compound of Formula (I).

The invention also relates to a method of treating or preventing a central nervous system disorder selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder, comprising administering to a subject in need thereof, a therapeutically effective amount of a compound of Formula (I) or a therapeutically effective amount of a pharmaceutical composition according to the invention.

The invention also relates to a product comprising a compound of Formula (I) and an additional pharmaceutical agent, as a combined preparation for simultaneous, separate or sequential use in the treatment or prevention of central nervous system conditions or diseases selected from mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

The present invention relates to novel 6,7-dihydropyrazolo[1,5-a]pyrazin-4(5H)-one derivatives designed to bind irreversibly to the mGluR2 receptor.

DETAILED DESCRIPTION OF THE INVENTION

The present invention relates in particular to compounds of Formula (I) as defined hereinabove, and stereoisomeric forms thereof, wherein
$R^1$ is phenyl or 2-pyridinyl, each optionally substituted with one or two substituents each independently selected from the group consisting of halo, $C_{1-4}$alkyl, monohalo-$C_{1-4}$alkyl, polyhalo-$C_{1-4}$alkyl, —$C_{1-4}$alkyl-O—$C_{1-4}$alkyl, monohalo-$C_{1-4}$alkyloxy, polyhalo-$C_{1-4}$alkyloxy, —$C_{1-4}$alkyl-OH, —CN, $C_{3-7}$cycloalkyl, and $SF_5$;
$R^2$ is selected from the group consisting of phenyl and pyridinyl, each of which is optionally substituted with one or two substituents each independently selected from the group consisting of halo, $C_{1-4}$alkyl, monohalo-$C_{1-4}$alkyl, polyhalo-$C_{1-4}$alkyl, —OH, —O—$C_{1-4}$alkyl, —$C_{1-4}$alkyl-O—$C_{1-4}$alkyl, monohalo-$C_{1-4}$alkyloxy, polyhalo-$C_{1-4}$alkyloxy, —$C_{1-4}$alkyl-OH, and $NR^{5a}R^{5b}$;
wherein $R^{5a}$ and $R^{5b}$ are each independently selected from hydrogen and $C_{1-4}$alkyl;
$R^3$ is selected from hydrogen and $C_{1-4}$alkyl;
$R^4$ is selected from the group consisting of hydrogen, $C_{1-4}$alkyl, monohalo-$C_{1-4}$alkyl, polyhalo-$C_{1-4}$alkyl, —$C_{1-4}$alkyl-O—$C_{1-4}$alkyl, and —$C_{1-4}$alkyl-OH;
and the N-oxides, and the pharmaceutically acceptable salts and the solvates thereof.

In an additional embodiment, the invention relates to compounds of Formula (I) as defined herein, and stereoisomeric forms thereof, wherein
$R^1$ is phenyl or 2-pyridinyl, each optionally substituted with one or two substituents each independently selected from the group consisting of halo, $C_{1-4}$alkyl, monohalo-$C_{1-4}$alkyl, polyhalo-$C_{1-4}$alkyl, —O—$C_{1-4}$alkyl, —$C_{1-4}$alkyl-O—$C_{1-4}$alkyl, monohalo-$C_{1-4}$alkyloxy, and polyhalo-$C_{1-4}$alkyloxy;
$R^2$ is selected from the group consisting of phenyl and pyridinyl, each of which is optionally substituted with one or two substituents each independently selected from the group consisting of halo, $C_{1-4}$alkyl, monohalo-$C_{1-4}$alkyl, polyhalo-$C_{1-4}$alkyl, —O—$C_{1-4}$alkyl, —$C_{1-4}$alkyl-O—$C_{1-4}$alkyl, monohalo-$C_{1-4}$alkyloxy, polyhalo-$C_{1-4}$alkyloxy, and $NR^{5a}R^{5b}$;
wherein $R^{5a}$ and $R^{5b}$ are each independently selected from hydrogen and $C_{1-4}$alkyl;
$R^3$ is hydrogen;
$R^4$ is selected from the group consisting of $C_{1-4}$alkyl, and —$C_{1-4}$alkyl-O—$C_{1-4}$alkyl; and the N-oxides, and the pharmaceutically acceptable salts and the solvates thereof.

In an additional embodiment, the invention relates to compounds of Formula (I) as defined herein, and stereoisomeric forms thereof, wherein
$R^1$ is phenyl or 2-pyridinyl, each optionally substituted with one or two substituents each independently selected from the group consisting of halo, polyhalo-$C_{1-4}$alkyl, and —O—$C_{1-4}$ alkyl;
$R^2$ is selected from the group consisting of phenyl and pyridinyl, each of which is optionally substituted with one or two substituents each independently selected from the group consisting of halo, $C_{1-4}$alkyl, —O—$C_{1-4}$alkyl, and $NR^{5a}R^{5b}$;
wherein $R^{5a}$ and $R^{5b}$ are each independently selected from hydrogen and $C_{1-4}$alkyl;
$R^3$ is hydrogen;
$R^4$ is $C_{1-4}$alkyl;
and the N-oxides, and the pharmaceutically acceptable salts and the solvates thereof.

In an additional embodiment, the invention relates to compounds of Formula (I) as defined herein, and stereoisomeric forms thereof, wherein
$R^1$ is phenyl optionally substituted with one or two substituents each independently selected from the group consisting of halo, polyhalo-$C_{1-4}$alkyl, and —O—$C_{1-4}$alkyl; or $R^1$ is 2-pyridinyl, optionally substituted with polyhalo-$C_{1-4}$alkyl;
$R^2$ is selected from the group consisting of phenyl and pyridinyl, wherein the pyridinyl is optionally substituted with one substituent selected from the group consisting of halo, $C_{1-4}$alkyl, —O—$C_{1-4}$alkyl, and $NR^{5a}R^{5b}$;
wherein $R^{5a}$ and $R^{5b}$ are each independently selected from hydrogen and $C_{1-4}$alkyl;
$R^3$ is hydrogen;
$R^4$ is $C_{1-4}$alkyl;
and the N-oxides, and the pharmaceutically acceptable salts and the solvates thereof.

In an additional embodiment, the invention relates to compounds of Formula (I) as defined herein, and stereoisomeric forms thereof, wherein $R^2$ is pyridinyl substituted with one $NH_2$; and $R^1$, $R^3$ and $R^4$ are as defined herein.

In an additional embodiment, the invention relates to compounds of Formula (I) as defined herein, and stereoisomeric forms thereof, wherein
$R^1$ is 4-(trifluoromethyl)phenyl or 3-chloro-4-(trifluoromethyl)phenyl;
$R^2$ is pyridinyl substituted with one $NH_2$;
>$CR^3R^4$ is >$CH(CH_3)$;
and the N-oxides, and the pharmaceutically acceptable salts and the solvates thereof.

In a further embodiment, the present invention relates to compounds of Formula (I) as defined herein wherein $R^3$ is hydrogen and $R^4$ is a substituent different from hydrogen having a configuration as depicted in the Formula (I') below, wherein the 6,7-dihydropyrazolo[1,5-a]pyrazin-4(5H)-one core, $R^1$ and $R^2$ are in the plane of the drawing and $R^4$ is projected above the plane of the drawing (bond shown with a bold wedge), and the rest of variables are as defined in Formula (I) herein

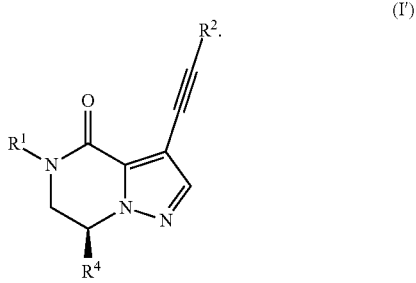

(I')

In a yet further embodiment, the present invention relates to compounds of Formula (I) as defined herein wherein $R^4$ is hydrogen and $R^3$ is a substituent different from hydrogen, for example a $C_{1-4}$alkyl substituent having a configuration as depicted in the Formula (I") below, wherein the 6,7-dihydropyrazolo[1,5-a]pyrazin-4(5H)-one core, $R^1$ and $R^2$ are in the plane of the drawing and $R^3$ is projected above the plane of the drawing (bond shown with a bold wedge), and the rest of variables are as defined in Formula (I) herein

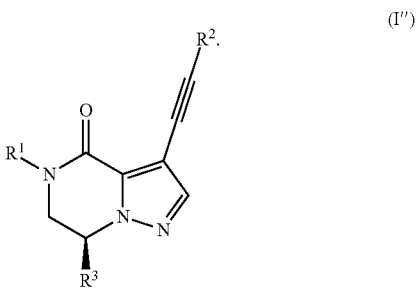

(I")

Specific compounds according to the invention include:
(7S)-3-[2-(6-amino-3-pyridyl)ethynyl]-7-methyl-5-[4-(trifluoromethyl)phenyl]-6,7-dihydropyrazolo[1,5-a]pyrazin-4-one;
(7S)-3-[2-(6-amino-3-pyridyl)ethynyl]-5-(3-chloro-4-methoxy-phenyl)-7-methyl-6,7-dihydropyrazolo[1,5-a]pyrazin-4-one;
(7S)-3-[2-(6-amino-3-pyridyl)ethynyl]-5-(3,4-dichlorophenyl)-7-methyl-6,7-dihydropyrazolo[1,5-a]pyrazin-4-one;
(7S)-3-[2-(6-amino-3-pyridyl)ethynyl]-7-methyl-5-[5-(trifluoromethyl)-2-pyridyl]-6,7-dihydropyrazolo[1,5-a]pyrazin-4-one;
(7S)-7-methyl-3-(2-phenylethynyl)-5-[4-(trifluoromethyl)phenyl]-6,7-dihydropyrazolo[1,5-a]pyrazin-4-one;
(7S)-7-methyl-3-[2-(2-methyl-4-pyridyl)ethynyl]-5-[4-(trifluoromethyl)phenyl]-6,7-dihydropyrazolo[1,5-a]pyrazin-4-one;
(7S)-7-methyl-3-[2-(6-methyl-3-pyridyl)ethynyl]-5-[4-(trifluoromethyl)phenyl]-6,7-dihydropyrazolo[1,5-a]pyrazin-4-one;
(7S)-3-[2-(2-amino-4-pyridyl)ethynyl]-7-methyl-5-[4-(trifluoromethyl)phenyl]-6,7-dihydropyrazolo[1,5-a]pyrazin-4-one;
(7S)-5-(3,4-dichlorophenyl)-3-[2-(6-methoxy-3-pyridyl)ethynyl]-7-methyl-6,7-dihydropyrazolo[1,5-a]pyrazin-4-one;
(7S)-5-(3,4-dichlorophenyl)-7-methyl-3-[2-[6-(methylamino)-3-pyridyl]ethynyl]-6,7-dihydropyrazolo[1,5-a]pyrazin-4-one;
(7S)-5-(3,4-dichlorophenyl)-3-[2-(6-fluoro-3-pyridyl)ethynyl]-7-methyl-6,7-dihydropyrazolo[1,5-a]pyrazin-4-one;
(7S)-5-(3,4-dichlorophenyl)-3-[2-[6-(dimethylamino)-3-pyridyl]ethynyl]-7-methyl-6,7-dihydropyrazolo[1,5-a]pyrazin-4-one;
(7S)-3-[2-(6-amino-3-pyridyl)ethynyl]-5-[3-chloro-4-(trifluoromethyl)phenyl]-7-methyl-6,7-dihydropyrazolo[1,5-a]pyrazin-4-one;
(7S)-3-[2-(6-amino-3-pyridyl)ethynyl]-5-[3-(hydroxymethyl)-4-(trifluoromethyl)phenyl]-7-methyl-6,7-dihydropyrazolo[1,5-a]pyrazin-4-one;
(7S)-3-[2-(6-amino-3-pyridyl)ethynyl]-5-[3-(fluoromethyl)-4-(trifluoromethyl)phenyl]-7-methyl-6,7-dihydropyrazolo[1,5-a]pyrazin-4-one;
(7S)-3-[2-(6-amino-3-pyridyl)ethynyl]-5-[6-methoxy-5-(trifluoromethyl)-2-pyridyl]-7-methyl-6,7-dihydropyrazolo[1,5-a]pyrazin-4-one
(7S)-5-[6-methoxy-5-(trifluoromethyl)-2-pyridyl]-7-methyl-3-[2-[6-(methylamino)-3-pyridyl]ethynyl]-6,7-dihydropyrazolo[1,5-a]pyrazin-4-one
(7S)-5-[6-chloro-5-(trifluoromethyl)-2-pyridyl]-7-methyl-3-[2-[6-(methylamino)-3-pyridyl]ethynyl]-6,7-dihydropyrazolo[1,5-a]pyrazin-4-one
(7S)-3-[2-[6-amino-5-(hydroxymethyl)-3-pyridyl]ethynyl]-7-methyl-5-[4-(trifluoromethyl)phenyl]-6,7-dihydropyrazolo[1,5-a]pyrazin-4-one
(7S)-3-[2-[6-amino-4-(hydroxymethyl)-3-pyridyl]ethynyl]-7-methyl-5-[4-(trifluoromethyl)phenyl]-6,7-dihydropyrazolo[1,5-a]pyrazin-4-one
(7S)-3-[2-[5-(hydroxymethyl)-3-pyridyl]ethynyl]-7-methyl-5-[4-(trifluoromethyl)phenyl]-6,7-dihydropyrazolo[1,5-a]pyrazin-4-one
(7S)-3-[2-[5-(methoxymethyl)-3-pyridyl]ethynyl]-7-methyl-5-[4-(trifluoromethyl)phenyl]-6,7-dihydropyrazolo[1,5-a]pyrazin-4-one
(7S)-3-[2-[5-(fluoromethyl)-3-pyridyl]ethynyl]-7-methyl-5-[4-(trifluoromethyl)phenyl]-6,7-dihydropyrazolo[1,5-a]pyrazin-4-one (7S)-3-[2-[6-amino-5-(fluoromethyl)-3-pyridyl]ethynyl]-7-methyl-5-[4-(trifluoromethyl)phenyl]-6,7-dihydropyrazolo[1,5-a]pyrazin-4-one (7S)-3-[2-[6-amino-5-(methoxymethyl)-3-pyridyl]ethynyl]-7-methyl-5-[4-(trifluoromethyl)phenyl]-6,7-dihydropyrazolo[1,5-a]pyrazin-4-one (7S)-3-[2-(6-amino-3-pyridyl)ethynyl]-5-[6-(fluoromethyl)-5-(trifluoromethyl)-2-pyridyl]-7-methyl-6,7-dihydropyrazolo[1,5-a]pyrazin-4-one (7S)-3-[2-(6-amino-3-pyridyl)ethynyl]-5-[3-fluoro-4-(trifluoromethyl)phenyl]-7-methyl-6,7-dihydropyrazolo[1,5-a]pyrazin-4-one (7S)-3-[2-(2-amino-3-pyridyl)ethynyl]-7-methyl-5-[4-(trifluoromethyl)phenyl]-6,7-dihydropyrazolo[1,5-a]pyrazin-4-one (7S)-3-[2-(6-amino-3-pyridyl)ethynyl]-7-methyl-5-[4-(1,2,2,2-tetrafluoroethyl)phenyl]-6,7-dihydropyrazolo[1,5-a]pyrazin-4-one (7S)-3-[2-[6-amino-4-(methoxymethyl)-3-pyridyl]ethynyl]-7-methyl-5-[4-(trifluoromethyl)phenyl]-6,7-dihydropyrazolo[1,5-a]pyrazin-4-one (7S)-7-methyl-3-[2-[2-(methylamino)-3-pyridyl]ethynyl]-5-[4-(trifluoromethyl)phenyl]-6,7-dihydropyrazolo[1,5-a]pyrazin-4-one (7S)-3-[2-[6-amino-4-(fluoromethyl)-3-pyridyl]ethynyl]-7-methyl-5-[4-(trifluoromethyl)phenyl]-6,7-dihydropyrazolo[1,5-a]pyrazin-4-one (7S)-3-[2-[6-amino-4-(hydroxymethyl)-3-pyridyl]ethynyl]-5-[3-chloro-4-(trifluoromethyl)phenyl]-7-methyl-6,7-dihydropyrazolo[1,5-a]pyrazin-4-one and the pharmaceutically acceptable salts and solvates of such compounds.

The present invention further relates to derivatives designed to bind irreversibly to the mGluR2 receptor, in particular to the allosteric pocket thereof.

In an embodiment, these compounds have the formula (I-a)

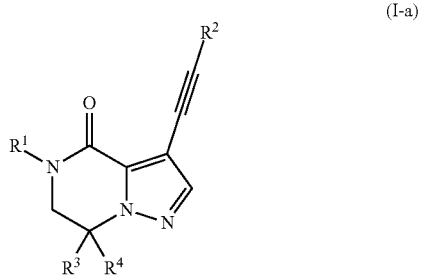

and stereoisomeric forms thereof, wherein
$R^1$ is phenyl or 2-pyridinyl, each optionally substituted with one or more substituents each independently selected from the group consisting of halo, $C_{1-4}$alkyl, monohalo-$C_{1-4}$alkyl, polyhalo-$C_{1-4}$alkyl, —$C_{1-4}$alkyl-OH, —CN, —$C_{1-4}$alkyl-O—$C_{1-4}$alkyl, $C_{3-7}$cycloalkyl, —O—$C_{1-4}$alkyl, monohalo-$C_{1-4}$alkyloxy, polyhalo-$C_{1-4}$alkyloxy, $SF_5$, $C_{1-4}$alkylthio, monohalo-$C_{1-4}$alkylthio and polyhalo-$C_{1-4}$alkylthio;
$R^2$ is phenyl substituted with —$S(O)_2F$;
$R^3$ is selected from hydrogen and $C_{1-4}$alkyl;
$R^4$ is selected from the group consisting of hydrogen, $C_{1-4}$alkyl, monohalo-$C_{1-4}$alkyl, polyhalo-$C_{1-4}$alkyl, —$C_{1-4}$alkyl-O—$C_{1-4}$alkyl, and —$C_{1-4}$alkyl-OH;
and the N-oxides, and the pharmaceutically acceptable salts and the solvates thereof.

The names of the compounds of the present invention were generated according to the nomenclature rules agreed upon by the International Union of Pure and Applied Chemistry (IUPAC) generated via Accelrys Direct Revision 8.0 SP1 (Microsoft Windows 64-bit Oracle11) (8.0.100.4) OpenEye:1.2.0. In case of tautomeric forms, the name of the depicted tautomeric form of the structure was generated. However it should be clear that the other non-depicted tautomeric form is also included within the scope of the present invention.

Definitions

The notation "$C_{1-4}$alkyl" as used herein alone or as part of another group, defines a saturated, straight or branched, hydrocarbon radical having, unless otherwise stated, from 1 to 4 carbon atoms, such as methyl, ethyl, 1-propyl, 1-methylethyl, butyl, 1-methyl-propyl, 2-methyl-1-propyl, 1,1-dimethylethyl and the like. The notation "—$C_{1-4}$alkyl-OH" as used herein alone or as part of another group, refers to $C_{1-4}$alkyl as defined before, substituted with one OH group at any available carbon atom.

The notation "halogen" or "halo" as used herein alone or as part of another group, refers to fluoro, chloro, bromo or iodo, with fluoro or chloro being preferred.

The notation "monohalo-$C_{1-4}$alkyl, polyhalo-$C_{1-4}$alkyl" as used herein alone or as part of another group, refers to $C_{1-4}$alkyl as defined before, substituted with 1, 2, 3 or where possible with more halo atoms as defined before.

The notation "$C_{3-7}$cycloalkyl" as used herein refers to a saturated, cyclic hydrocarbon radical having from 3 to 7 carbon atoms, such as cyclopropyl, cyclobutyl, cyclopentyl, cyclohexyl and cycloheptyl. A particular $C_{3-7}$cycloalkyl group is cyclopropyl.

The N-oxide forms of the compounds according to Formula (I) are meant to comprise those compounds of Formula (I) wherein one or several nitrogen atoms are oxidized to the so called N-oxide, particularly those N-oxides wherein a nitrogen atom in a pyridinyl radical is oxidized. N-oxides can be formed following procedures known to the skilled person. The N-oxidation reaction may generally be carried out by reacting the starting material of Formula (I) with an appropriate organic or inorganic peroxide. Appropriate inorganic peroxides comprise, for example, hydrogen peroxide, alkali metal or alkaline metal peroxides, e.g. sodium peroxide, potassium peroxide/appropriate organic peroxides may comprise peroxy acids such as, for example, benzenecarboperoxoic acid or halo substituted benzenecarboperoxoic acid, e.g. 3-chloroperoxybenzoic acid (or 3-chloroperbenzoic acid), peroxoalkanoic acids, e.g. peroxoacetic acid, alkylhydroperoxides, e.g. tert-butyl hydroperoxide. Suitable solvents, are for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Whenever the term "substituted" is used in the present invention, it is meant, unless otherwise is indicated or is clear from the context, to indicate that one or more hydrogens, preferably from 1 to 3 hydrogens, more preferably from 1 to 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

It will be appreciated that some of the compounds of Formula (I) and their pharmaceutically acceptable addition salts and solvates thereof may contain one or more centres of chirality and exist as stereoisomeric forms.

The term "compounds of the invention" as used herein, is meant to include the compounds of Formula (I), and the salts and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic (partially) saturated radicals may have either the cis- or trans-configuration; for example if a compound contains a disubstituted cycloalkyl group, the substituents may be in the cis or trans configuration.

Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above formula are intended to be included within the scope of the present invention.

It follows that a single compound may exist in both stereoisomeric and tautomeric forms.

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the solvent addition forms as well as the salts thereof, which the compounds of Formula (I) are able to form. Examples of such solvent addition forms are e.g. hydrates, alcoholates and the like.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form, for example $^2$H.

Radiolabelled compounds of Formula (I) may comprise a radioactive isotope selected from the group consisting of $^3$H, $^{11}$C, $^{14}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group consisting of $^3$H, $^{11}$C and $^{18}$F.

Preparation

The compounds according to the invention can generally be prepared by a succession of steps, each of which is known to the skilled person. In particular, the compounds can be prepared according to the following synthesis methods.

The compounds of Formula (I) may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase or chiral supercritical fluid chromatography (SFC). Said pure stereochemically isomeric forms may also be derived from the corresponding pure stereochemically isomeric forms of the appropriate starting materials, provided that the reaction occurs stereospecifically. The absolute configuration of compounds of the invention reported herein was determined by analysis of the racemic mixture by supercritical fluid chromatography (SFC) followed by SFC comparison of the separate enantiomer(s) which were obtained by asymmetric synthesis, followed by vibrational circular dichroism (VCD) analysis of the particular enantiomer(s).

A. Preparation of the Final Compounds

Experimental Procedure 1

Final compounds according to Formula (I) can be prepared by a Sonogashira type coupling reaction of a compound of Formula (II) with an appropriate acetylene of Formula (V) according to reaction conditions known to the skilled person. Such reaction conditions include the use of a palladium catalyst, such as bis(triphenylphosphine)palladium(II) chloride, and a copper(I) catalyst such as copper(I) iodide in the presence of a base, such as triethylamine, in a suitable solvent, such as N,N-dimethylformamide, under suitable reaction conditions such as, degassing the reaction mixture with an inert gas, such as nitrogen, and under suitable reaction conditions, such as at a convenient temperature, in particular 55° C., for a period of time to ensure the completion of the reaction. A compound of Formula (V) can be obtained commercially or made according to procedures known in the art. In Reaction Scheme 1, halo is defined as bromo or iodo and all other variables are defined as in Formula (I).

Reaction Scheme 1

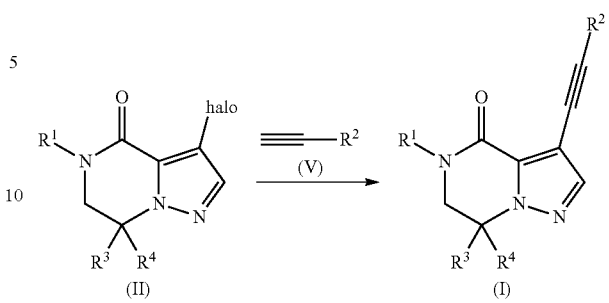

Experimental Procedure 2

Alternatively, final compounds according to Formula (I) can be prepared by a Sonogashira type coupling reaction of a compound of Formula (III) with an appropriate aryl/heteroaryl halide of Formula (VI) where X is halo, in particular bromo or iodo, according to conditions known to the skilled person. Such reaction conditions include the use of a palladium catalyst, such as bis(triphenylphosphine) palladium(II) chloride, and a copper(I) catalyst such as copper(I) iodide in the presence of a base, such as triethylamine, in a suitable solvent, such as N,N-dimethylformamide, under suitable reaction conditions such as, degassing the reaction mixture with an inert gas, such as nitrogen, and under suitable reaction conditions, such as at a convenient temperature, in particular 55° C., for a period of time to ensure the completion of the reaction. A compound of Formula (VI) can be obtained commercially or made according to procedures known in the art. In Reaction Scheme 2, all other variables are defined as in Formula (I).

Reaction Scheme 2

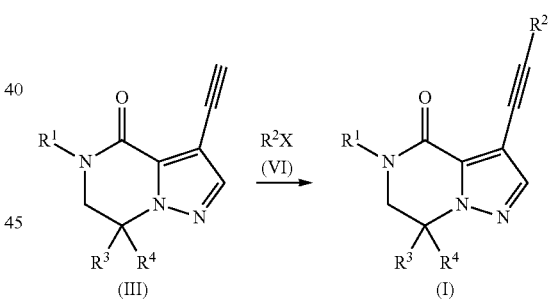

Experimental Procedure 3

Alternatively, final compounds according to Formula (I) can be prepared by a Goldberg coupling reaction of a compound of Formula (IV) with an appropriate aryl/heteroaryl halide of Formula (VII) where X is halo, in particular bromo or iodo, according to conditions known to the skilled person. Such conditions for example include the use of a suitable copper catalyst such as copper(I) iodide, in the presence of a ligand such as (+/−)-trans-1,2-cyclohexanediamine, in the presence of a suitable base such as K$_3$PO$_4$ in a suitable solvent such as 1,4-dioxane, under suitable reaction conditions, such as at a convenient temperature, typically ranging between 80° C. and 120° C., in particular 100° C., for a period of time to ensure the completion of the reaction. A compound of Formula (VII) can be obtained commercially or made according to procedures known in the art. In Reaction Scheme 3, all other variables are defined as in Formula (I).

Reaction Scheme 3

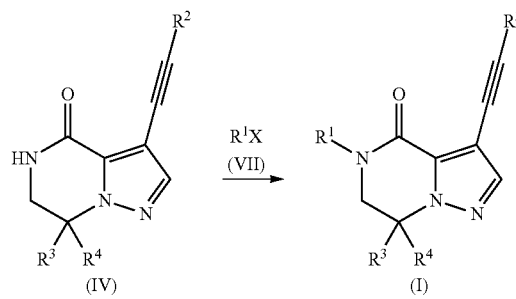

Experimental Procedure 4

Alternatively, final compounds according to Formula (I) can be prepared by a reaction of fluorination of a compound of Formula (I-a) wherein $R^{1'}$ is phenyl or 2-pyridinyl substituted with $C_{1-4}$alkyl-OH. A compound of Formula (Ia) can be treated in the presence of a fluorinating agent such as for example (diethylamino)sulfur trifluoride in a suitable solvent such as, for example DCM, and stirring the reaction mixture at 0° C. for a period of time to ensure the completion of the reaction. In Reaction Scheme 4, all variables are defined as in Formula (I).

Reaction Scheme 4

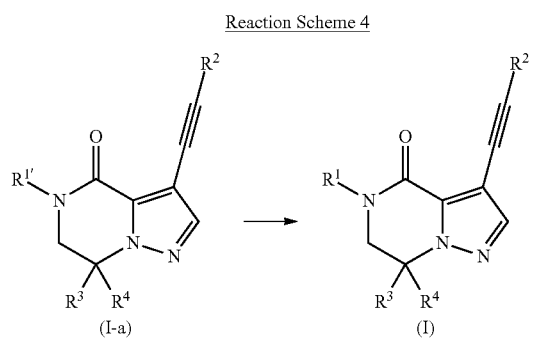

Experimental Procedure 5

Alternatively, final compounds according to Formula (I) by a reaction of substitution of a compound of Formula (I-b) wherein $R^{2'}$ is selected from 2-halo-pyridinyl group. A compound of Formula (I-b) can be treated with an amine or an alcohol, in a suitable solvent such as, for example ethanol (EtOH) or tetrahydrofuran (THF), under suitable reaction conditions, such as heating under microwave irradiation, at a convenient temperature, in particular at 130° C., for a period of time to ensure the completion of the reaction. In Reaction Scheme 5, all variables are defined as in Formula (I).

Reaction Scheme 5

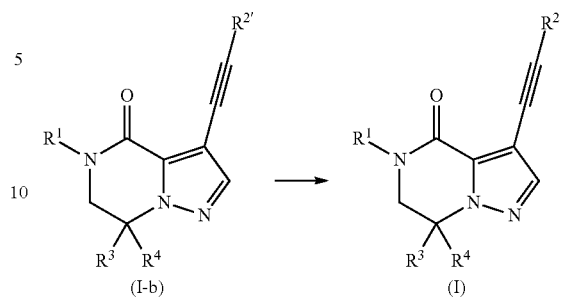

B. Preparation of the Intermediate Compounds

Experimental Procedure 6

Intermediate compounds according to Formula (II) can be prepared via a reaction of halogenation of an intermediate of Formula (VIII) with a halogenating reagent such as iodine, in the presence of ammonium cerium(IV) nitrate and in an inert solvent such as acetonitrile, under suitable reaction conditions, such as at a convenient temperature, typically 70° C., for a period of time to ensure the completion of the reaction.

Intermediate compounds according to Formula (VIII) can be prepared by a Goldberg reaction of an intermediate compound of Formula (IX) with an appropriate aryl/heteroaryl halide of Formula (VII) where X is halo with a suitable copper(I) catalyst such as copper(I) iodide, in the presence of a ligand, such as N,N-dimethylethylenediamine, in the presence of a base, such as sodium carbonate, in a suitable solvent, such as toluene or a mixture of toluene and N,N-dimethylformamide, under suitable reaction conditions, such as at a convenient temperature, typically ranging between 100° C. and 140° C., for a period of time to ensure the completion of the reaction. An intermediate compound of Formula (VII) can be obtained commercially or made according to procedures known in the art.

In Reaction Scheme 6, halo is defined as iodo or bromo and all other variables are defined as in Formula (I).

Reaction Scheme 6

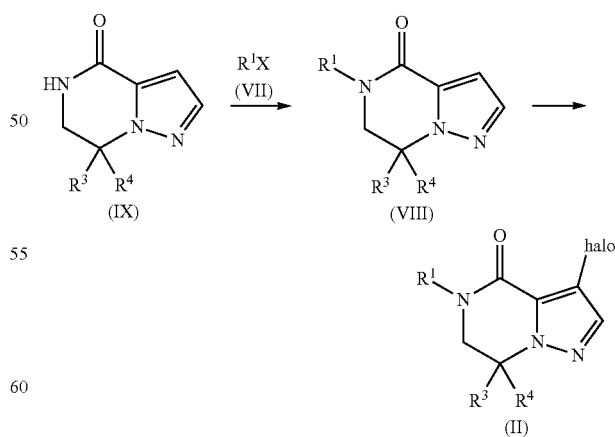

Experimental Procedure 7

Intermediate compounds according to Formula (III) can be prepared by a deprotection reaction of a compound of Formula (X) according to conditions known to the skilled person. A compound of Formula (III) can be obtained by removal of the protecting group in (X) such as for example trimethylsilane protecting group, in the presence of basic media, such as potassium carbonate in an inert solvent such as methanol or mixture of methanol and ethyl acetate, under suitable reaction conditions, such as at a convenient temperature, typically room temperature, for a period of time to ensure the completion of the reaction.

Intermediate compounds according to Formula (X) can be prepared by a Sonogashira type coupling reaction of a compound of Formula (II) with trimethylsilylacetylene according to reaction conditions known to the skilled person. Such reaction conditions include the use of a palladium catalyst, such as bis(triphenylphosphine)palladium(II) chloride, and a copper(I) catalyst such as copper(I) iodide in the presence of a base, such as triethylamine, in a suitable solvent, such as N,N-dimethylformamide, under suitable reaction conditions such as, degassing the reaction mixture with an inert gas, such as nitrogen, and under suitable reaction conditions, such as at a convenient temperature, in particular 55° C., for a period of time to ensure the completion of the reaction.

In Reaction Scheme 7, halo is defined as iodo or bromo and all other variables are defined as in Formula (I)

Reaction Scheme 7

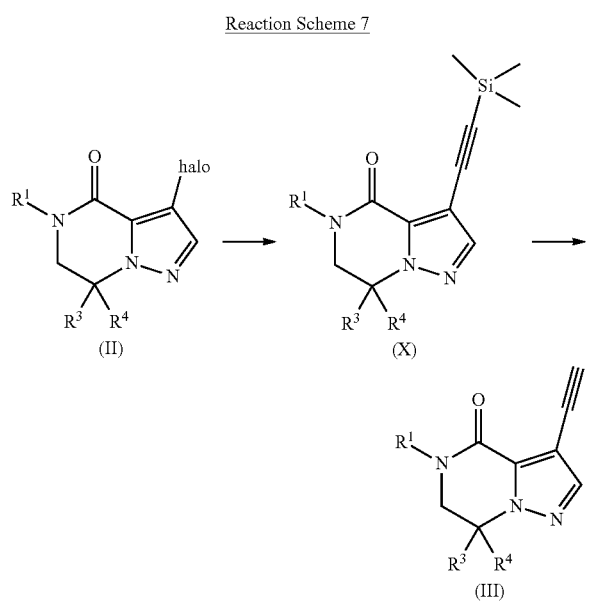

Experimental Procedure 8

Intermediate compounds according to Formula (IV) can be prepared by a Sonogashira type coupling reaction of a compound of Formula (XI) with an appropriate acetylene of Formula (V) according to reaction conditions known to the skilled person. Such reaction conditions include the use of a palladium catalyst, such as bis(triphenylphosphine)palladium(II) chloride, and a copper(I) catalyst such as copper(I) iodide in the presence of a base, such as triethylamine, in a suitable solvent, such as N,N-dimethylformamide, under suitable reaction conditions such as, degassing the reaction mixture with an inert gas, such as nitrogen, and under suitable reaction conditions, such as at a convenient temperature, in particular 55° C., for a period of time to ensure the completion of the reaction.

Intermediate compounds according to Formula (XI) can be prepared via a reaction of halogenation of an intermediate of Formula (IX) with a halogenating reagent such as iodine, in the presence of ammonium cerium(IV) nitrate and in an inert solvent such as acetonitrile, under suitable reaction conditions, such as at a convenient temperature, typically 70° C., for a period of time to ensure the completion of the reaction.

In Reaction Scheme 8, halo is defined as iodo or bromo and all other variables are defined as in Formula (I).

Reaction Scheme 8

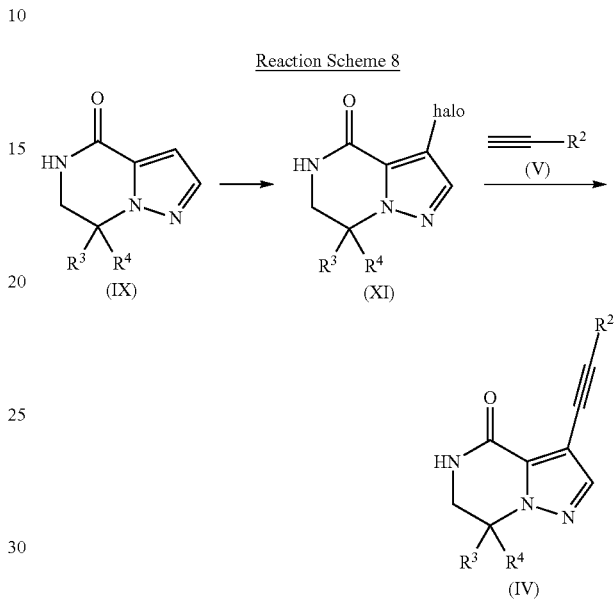

Experimental Procedure 9

Intermediate compound of Formula (IX) can be prepared by removal of the protecting group for example a tert-butoxycarbonyl group, in an intermediate of Formula (XII), for example in the presence of acidic media, such as hydrochloric acid, in an inert solvent such as 1,4-dioxane, under suitable reaction conditions, such as at a convenient temperature, typically 80° C., for a period of time to ensure the completion of the reaction followed by treatment with a base, such as sodium carbonate or sodium bicarbonate, under suitable reaction conditions, such as at a convenient temperature, typically ranging between 0° C. and 40° C., for a period of time to ensure the completion of the reaction.

Intermediate compound of Formula (XII) wherein $R^6$ is $C_{1-4}$alkyl and PG is a protecting group, for example a tert-butoxycarbonyl group, can be prepared by a Mitsunobu type reaction between a compound of Formula (XIII) and an appropriate alcohol of Formula (XIV), in the presence of a suitable triarylphosphine, such as triphenylphosphine, or a suitable trialkylphosphine, and a suitable dialkyl azodicarboxylate reagent, such as di-tert-butyl azodicarboxylate, in a suitable inert solvent, such as tetrahydrofuran, under suitable reaction conditions, such as at a convenient temperature, typically room temperature, for a period of time to ensure the completion of the reaction.

Intermediate compounds of Formula (XIII) or Formula (XIV) can be obtained commercially or synthesized according to literature procedures. In Reaction Scheme 9, $R^6$ is $C_{1-4}$alkyl, PG is a protecting group and all other variables are defined as in Formula (I).

Reaction Scheme 9

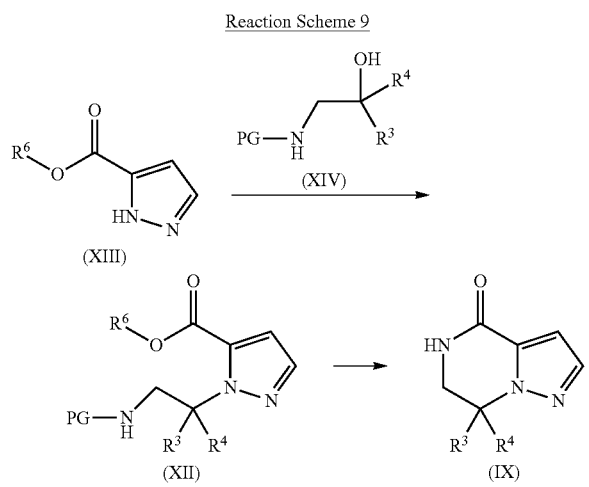

In order to obtain the HCl salt forms of the compounds, several procedures known to those skilled in the art can be used. In a typical procedure, for example, the free base can be dissolved in DIPE or $Et_2O$ and subsequently, a 6N HCl solution in 2-propanol or a 1N HCl solution in $Et_2O$ can be added dropwise. The mixture typically is stirred for 10 minutes after which the product can be filtered off. The HCl salt usually is dried in vacuo.

It will be appreciated by those skilled in the art that in the processes described above the functional groups of intermediate compounds may need to be blocked by protecting groups. In case the functional groups of intermediate compounds were blocked by protecting groups, they can be deprotected after a reaction step.

Pharmacology

The compounds provided in this invention are negative allosteric modulators (NAMs) of metabotropic glutamate receptors, in particular they are negative allosteric modulators of mGluR2. The compounds of the present invention do not appear to bind to the glutamate recognition site, the orthosteric ligand site, but instead to an allosteric site within the seven transmembrane region of the receptor. In the presence of glutamate, the compounds of this invention decrease the mGluR2 response. The compounds provided in this invention are expected to have their effect at mGluR2 by virtue of their ability to decrease the response of such receptors to glutamate, attenuating the response of the receptor.

As used herein, the term "treatment" is intended to refer to all processes, wherein there may be a slowing, interrupting, arresting or stopping of the progression of a disease or an alleviation of symptoms, but does not necessarily indicate a total elimination of all symptoms.

Hence, the present invention relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof for use as a medicament.

The invention also relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for the manufacture of a medicament.

The invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for use in the treatment or prevention of, in particular treatment of, a condition in a mammal, including a human, the treatment or prevention of which is affected or facilitated by the neuromodulatory effect of allosteric modulators of mGluR2, in particular negative allosteric modulators thereof.

The present invention also relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for the manufacture of a medicament for the treatment or prevention of, in particular treatment of, a condition in a mammal, including a human, the treatment or prevention of which is affected or facilitated by the neuromodulatory effect of allosteric modulators of mGluR2, in particular negative allosteric modulators thereof.

The present invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for use in the treatment, prevention, amelioration, control or reduction of the risk of various neurological and psychiatric disorders associated with glutamate dysfunction in a mammal, including a human, the treatment or prevention of which is affected or facilitated by the neuromodulatory effect of negative allosteric modulators of mGluR2.

Also, the present invention relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, or a pharmaceutical composition according to the invention for the manufacture of a medicament for treating, preventing, ameliorating, controlling or reducing the risk of various neurological and psychiatric disorders associated with glutamate dysfunction in a mammal, including a human, the treatment or prevention of which is affected or facilitated by the neuromodulatory effect of negative allosteric modulators of mGluR2.

In particular, the neurological and psychiatric disorders associated with glutamate dysfunction, include one or more of the following central nervous system conditions or diseases: mood disorders; delirium, dementia, amnestic and other cognitive disorders; disorders usually first diagnosed in infancy, childhood or adolescence; substance-related disorders; schizophrenia and other psychotic disorders; somatoform disorders; and hypersomnic sleep disorder.

In particular, the central nervous system disorder is a psychotic disorder selected from the group of schizophrenia (in particular in antipsychotic-stabilized patients), schizophreniform disorder, schizoaffective disorder, delusional disorder, brief psychotic disorder, and substance-induced psychotic disorder.

In particular, the central nervous system disorder is a substance-related disorder selected from the group of alcohol dependence, alcohol abuse, amphetamine dependence, amphetamine abuse, caffeine dependence, caffeine abuse, cannabis dependence, cannabis abuse, cocaine dependence, cocaine abuse, hallucinogen dependence, hallucinogen abuse, nicotine dependence, nicotine abuse, opioid dependence, opioid abuse, phencyclidine dependence, and phencyclidine abuse.

In particular, the central nervous system disorder is a mood disorder selected from the group of major depressive disorder, depression, treatment resistant depression, dysthymic disorder, cyclothymic disorder, and substance-induced mood disorder.

In particular, the central nervous system disorder is a disorder usually first diagnosed in infancy, childhood, or adolescence selected from mental retardation, learning disorder, motor skills disorder, communication disorder, attention-deficit and disruptive behaviour disorders (such as Attention-Deficit/Hyperactivity Disorder (ADHD)). An additional disorder usually first diagnosed in infancy, childhood, or adolescence is autistic disorder.

In particular, the central nervous system disorder is a cognitive disorder selected from the group of dementia, in particular, dementia of the Alzheimer's type, vascular dementia, dementia due to HIV disease, dementia due to head trauma, dementia due to Parkinson's disease, dementia due to Huntington's disease, dementia due to Pick's disease, dementia due to Creutzfeldt-Jakob disease, and substance-induced persisting dementia.

In particular, the central nervous system disorder is an amnestic disorder, such as substance-induced persisting amnestic disorder.

As already mentioned hereinabove, the term "treatment" does not necessarily indicate a total elimination of all symptoms, but may also refer to symptomatic treatment in any of the disorders mentioned above. In particular, symptoms that may be treated include but are not limited to, memory impairment in particular in dementia or in major depressive disorder, age-related cognitive decline, mild cognitive impairment, and depressive symptoms.

Of the disorders mentioned above, the treatment of dementia, major depressive disorder, depression, treatment resistant depression, attention-deficit/hyperactivity disorder and schizophrenia, in particular in antipsychotic-stabilized patients, are of particular importance.

The fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

A skilled person will be familiar with alternative nomenclatures, nosologies, and classification systems for the diseases or conditions referred to herein. For example, the "American Psychiatric Association: Diagnostic and Statistical Manual of Mental Disorders, Fifth Edition. Arlington, Va., American Psychiatric Association, 2013" (DSM-5™) utilizes terms such as depressive disorders, in particular, major depressive disorder, persistent depressive disorder (dysthymia), substance-medication-induced depressive disorder; neurocognitive disorders (NCDs) (both major and mild), in particular, neurocognitive disorders due to Alzheimer's disease, vascular NCD (such as vascular NCD present with multiple infarctions), NCD due to HIV infection, NCD due to traumatic brain injury (TBI), NCD due to Parkinson's disease, NCD due to Huntington's disease, frontotemporal NCD, NCD due to prion disease, and substance/medication-induced NCD; neurodevelopmental disorders, in particular, intellectual disability, specific learning disorder, neurodevelopmental motor disorder, communication disorder, and attention-deficit/hyperactivity disorder (ADHD); substance-related disorders and addictive disorders, in particular, alcohol use disorder, amphetamine use disorder, cannabis use disorder, cocaine use disorder, other hallucinogen use disorder, tobacco use disorder, opioid use disorder, and phencyclidine use disorder; schizophrenia spectrum and other psychotic disorders, in particular, schizophrenia, schizophreniform disorder, schizoaffective disorder, delusional disorder, brief psychotic disorder, substance/medication-induced psychotic disorder; somatic symptom disorders; hypersomnolence disorder; and cyclothymic disorder (which under DSM-5™ falls under the bipolar and related disorders category). Such terms may be used by the skilled person as an alternative nomenclature for some of the diseases or conditions referred to herein. An additional neurodevelopmental disorder includes autism spectrum disorder (ASD), which encompasses according to the DSM-5™, disorders previously known by the terms early infantile autism, childhood autism, Kanner's autism, high-functioning autism, atypical autism, pervasive developmental disorder not otherwise specified, childhood disintegrative disorder, and Asperger's disorder. In particular, the disorder is autism. Specifiers associated with ASD include those where the individual has a genetic disorder, such as in Rett syndrome or Fragile X syndrome.

Therefore, the invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for use in the treatment of any one of the diseases mentioned hereinbefore.

The invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for use in treating any one of the diseases mentioned hereinbefore.

The invention also relates to a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for the treatment or prevention, in particular treatment, of any one of the diseases mentioned hereinbefore.

The invention also relates to the use of a compound according to the general Formula (I), or a stereoisomeric form thereof, or an N-oxide thereof, or a pharmaceutically acceptable salt or a solvate thereof, in particular, a compound of Formula (I) or a stereoisomeric form thereof, or a pharmaceutically acceptable salt or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), there is provided a method of treating warm-blooded animals, including humans, suffering from any one of the diseases mentioned hereinbefore, and a method of preventing in warm-blooded animals, including humans, any one of the diseases mentioned hereinbefore.

Said methods comprise the administration, i.e. the systemic or topical administration, preferably oral administration, of a therapeutically effective amount of a compound of Formula (I), a stereoisomeric form thereof, or an N-oxide thereof, or a pharmaceutically acceptable salt or solvate thereof, in particular, a compound of Formula (I) or a stereoisomeric form thereof, or a pharmaceutically acceptable salt or a solvate thereof, to warm-blooded animals, including humans.

Therefore, the invention also relates to a method for the prevention and/or treatment of any one of the diseases mentioned hereinbefore comprising administering a therapeutically effective amount of a compound according to the invention to a subject in need thereof.

One skilled in the art will recognize that a therapeutically effective amount of the NAMs of the present invention is the amount sufficient to modulate the activity of the mGluR2 and that this amount varies inter alia, depending on the type of disease, the concentration of the compound in the therapeutic formulation, and the condition of the patient. Generally, an amount of NAM to be administered as a therapeutic agent for treating diseases in which modulation of the mGluR2 is beneficial, such as the disorders described herein, will be determined on a case by case by an attending physician.

Generally, a suitable dose is one that results in a concentration of the NAM at the treatment site in the range of 0.5 nM to 200 µM, and more usually 5 nM to 50 µM. To obtain these treatment concentrations, a patient in need of treatment likely will be administered an effective therapeutic daily amount of about 0.01 mg/kg to about 50 mg/kg body weight, preferably from about 0.01 mg/kg to about 25 mg/kg body weight, more preferably from about 0.01 mg/kg to about 10 mg/kg body weight, more preferably from about 0.01 mg/kg to about 2.5 mg/kg body weight, even more preferably from about 0.05 mg/kg to about 1 mg/kg body weight, more preferably from about 0.1 to about 0.5 mg/kg body weight. The amount of a compound according to the present invention, also referred to here as the active ingredient, which is required to achieve a therapeutically effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

The compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone. Examples of such combinations include the compounds of the invention in combination with antipsychotic(s), NMDA receptor antagonists (e.g. memantine), NR2B antagonists, acetylcholinesterase inhibitors (e.g. donepezil, galantamine, physostigmine and rivastigmine) and/or antidepressant neurotransmitter reuptake inhibitors. Particular combinations include the compounds of the invention in combination with antipsychotics, or the compounds of the invention in combination with memantine and/or NR2B antagonists.

Pharmaceutical Compositions

The present invention also provides compositions for preventing or treating diseases in which modulation of the mGluR2 receptor is beneficial, such as the disorders described herein. While it is possible for the active ingredient to be administered alone, it is preferable to present it as a pharmaceutical composition. Accordingly, the present invention also relates to a pharmaceutical composition comprising a pharmaceutically acceptable carrier or diluent and, as active ingredient, a therapeutically effective amount of a compound according to the invention, in particular a compound according to Formula (I), an N-oxide, a pharmaceutically acceptable salt thereof, a solvate thereof or a stereochemically isomeric form thereof, more in particular, a compound according to Formula (I), a pharmaceutically acceptable salt thereof, a solvate thereof or a stereochemically isomeric form thereof. The carrier or diluent must be "acceptable" in the sense of being compatible with the other ingredients of the composition and not deleterious to the recipients thereof.

The compounds according to the invention, in particular the compounds according to Formula (I), the N-oxides thereof, the pharmaceutically acceptable salts thereof, the solvates and the stereochemically isomeric forms thereof, more in particular the compounds according to Formula (I), the pharmaceutically acceptable salts thereof, the solvates and the stereochemically isomeric forms thereof, or any subgroup or combination thereof may be formulated into various pharmaceutical forms for administration purposes. As appropriate compositions there may be cited all compositions usually employed for systemically administering drugs.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). To prepare the pharmaceutical compositions of this invention, a therapeutically effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for oral, topical, rectal or percutaneous administration, by parenteral injection or by inhalation. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of the ease in administration, oral administration is preferred, and tablets and capsules represent the most advantageous oral dosage unit forms in which case solid pharmaceutical carriers are obviously employed. For parenteral compositions, the carrier will usually comprise sterile water, at least in large part, though other ingredients, for example, surfactants, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, teaspoonfuls, tablespoonfuls, and segregated multiples thereof.

Since the compounds according to the invention are orally administrable compounds, pharmaceutical compositions comprising aid compounds for oral administration are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

As already mentioned, the invention also relates to a pharmaceutical composition comprising the compounds according to the invention and one or more other drugs for use as a medicament or for use in the treatment, prevention, control, amelioration, or reduction of risk of diseases or conditions for which compounds of Formula (I) or the other drugs may have utility. The use of such a composition for the manufacture of a medicament as well as the use of such a composition for the manufacture of a medicament in the treatment, prevention, control, amelioration or reduction of risk of diseases or conditions for which compounds of Formula (I) or the other drugs may have utility are also contemplated. The present invention also relates to a combination of a compound according to the present invention and an additional drug selected from the group of antipsychotics; NMDA receptor antagonists (e.g. memantine); NR2B antagonists; acetylcholinesterase inhibitors (e.g. donepezil, galantamine, physostigmine and rivastigmine) and/or antidepressant neurotransmitter reuptake inhibitors. In particular, the present invention also relates to a combination of a compound according to the present invention and antipsychotic(s), or to a combination of a compound according to the present invention and memantine and/or an NR2B antagonist. The present invention also relates to such a combination for use as a medicine. The present invention also relates to a product comprising (a) a compound according to the present invention, an N-oxide thereof, a pharmaceutically acceptable salt thereof or a solvate thereof, in particular, a pharmaceutically acceptable salt thereof or a solvate thereof, and (b) an additional component selected from antipsychotics, NMDA receptor antagonists (e.g. memantine), NR2B antagonists, acetylcholinesterase inhibitors and/or antidepressant neurotransmitter reuptake inhibitor(s), as a combined preparation for simultaneous, separate or sequential use in the treatment or prevention of a condition in a mammal, including a human, the treatment or prevention of which is affected or facilitated by the neuromodulatory effect of mGluR2 allosteric modulators, in particular negative mGluR2 allosteric modulators. More in particular the additional component (b) is selected from antipsychotic(s) or memantine and/or an NR2B antagonist. The different drugs of such a combination or product may be combined in a single preparation together with pharmaceutically acceptable carriers or diluents, or they may each be present in a separate preparation together with pharmaceutically acceptable carriers or diluents.

The following examples are intended to illustrate but not to limit the scope of the present invention.

Chemistry

Several methods for preparing the compounds of this invention are illustrated in the following Examples. Unless otherwise noted, all starting materials were obtained from commercial suppliers and used without further purification.

Hereinafter, "CI" means chemical ionisation; "CSH" means charged surface hybrid; "DAD" means diode-array detector; "THF" means tetrahydrofuran; "Et$_3$N" means triethylamine; "DIPE" means diisopropylether; "DMF" means N,N-dimethylformamide; "Et$_2$O" means diethylether; "EtOAc" means ethyl acetate; "DCM" means dichloromethane; "DMSO" means dimethylsulfoxide; "L" means liter; "LRMS" means low-resolution mass spectrometry/spectra; "HPLC" means high performance liquid chromatography; "HRMS" means high-resolution mass spectrometry/spectra; "mL" or "ml" means milliliter; "NH$_4$Ac" means ammonium acetate; "EtOH" means ethanol; "ES" means electrospray; "Xantphos" means 4,5-Bis(diphenylphosphino)-9,9-dimethylxanthene; "MeOH" means methanol; "eq" means equivalent(s); "RP" means Reverse Phase; "rt" or "RT" mean room temperature; "M.p." means melting point; "min" means minutes; "h" means hour(s); "RRHD" means Rapid Resolution High Definition; "s" means second(s); "TOF" means time of flight; "sat." means saturated; "QTOF" means Quadrupole-Time of Flight; "SFC" means supercritical fluid chromatography; "sol." means solution; "SQD" means Single Quadrupole Detector; "UPLC" means Ultra Performance Liquid Chromatography.

Microwave assisted reactions were performed in a single-mode reactor: Initiator™ Sixty EXP microwave reactor (Biotage AB), or in a multimode reactor: MicroSYNTH Labstation (Milestone, Inc.).

Thin layer chromatography (TLC) was carried out on silica gel 60 F254 plates (Merck) using reagent grade solvents. Open column chromatography was performed on silica gel, particle size 60 Å, mesh=230-400 (Merck) using standard techniques. Automated flash column chromatography was performed using ready-to-connect cartridges on irregular silica gel (normal phase disposable flash columns) from different vendors on different flash systems.

Nuclear Magnetic Resonance (NMR): For a number of compounds, $^1$H NMR spectra were recorded either on a Bruker Avance III, on a Bruker DPX-400 or on a Bruker AV-500 spectrometer with standard pulse sequences, operating at 400 MHz and 500 MHz, respectively. Chemical shifts ($\delta$) are reported in parts per million (ppm) downfield from tetramethylsilane (TMS), which was used as internal standard.

Synthesis of Intermediate Compounds

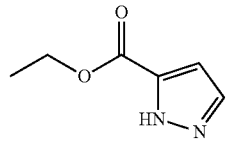

Intermediate 1 (I-1)

Sulfuric acid (10 mL, 187.6 mmol) was added to a solution of 1-H-pyrazole-3-carboxylic acid (1.93 g, 17.22 mmol) in EtOH (20 mL). The mixture was stirred at 90° C. for 15 h. Then it was allowed to cool to rt and the solvents were evaporated in vacuo. The residue was poured into water and the solution basified with K$_2$CO$_3$ and extracted with EtOAc. The organic layer was separated, dried (MgSO$_4$), filtered and the solvent evaporated in vacuo to yield intermediate compound I-1 as a white solid (2.28 g, 93% purity, 94%) which was used in the following step without further purification.

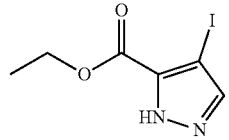

Intermediate 2 (I-2)

Intermediate I-1 (100 g, 0.68 mol), N-iodosuccinimide (213.5 g, 0.95 mol) were dissolved in DCM (2 L). The mixture was stirred at rt for 24 h. The mixture was treated with a sat. sol. of Na$_2$S$_2$O$_3$ and a sat. sol. of Na$_2$CO$_3$ and extracted with DCM. The organic layer was separated, dried (MgSO$_4$), filtered and the solvent evaporated in vacuo to yield intermediate compound I-2 as a white solid (160 g, 85%).

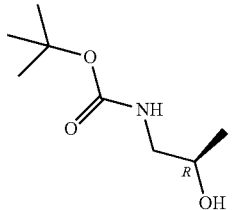

Intermediate 3 (I-3)

Di-tert-butyl dicarbonate (58.1 g, 266.3 mmol) in DCM (50 mL) was added to a stirred solution of (R)-(−)-1-amino-2-propanol in DCM (50 mL) at 0° C. under nitrogen. The mixture was stirred at rt for 2 h. The mixture was diluted with cooled water and extracted with DCM. The organic layer was separated, dried (Na$_2$SO$_4$), filtered and the solvents evaporated in vacuo to yield intermediate I-3 as a colorless oil (47 g, quant.). The product was used in the next step without further purification.

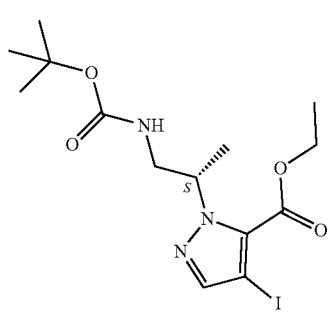

Intermediate 4 (I-4)

Di-tert-butyl azodicarboxylate (4.67 g, 20.3 mmol) was added to a stirred solution of intermediate I-2 (3 g, 11.28 mmol), intermediate I-3 (4.44 g, 22.55 mmol) and triphenylphosphine (5.32 g, 20.3 mmol) in THF (56 mL) under nitrogen. The mixture was stirred at rt for 5 h. The solvent was evaporated in vacuo and the crude product was triturated with DIPE. The solid was filtered and the filtrate was evaporated in vacuo. The crude product was purified by flash column chromatography (silica; EtOAc in Heptane 0/100 to 30/70). The desired fractions were collected and the solvents evaporated in vacuo to give intermediate compound I-4 as a colorless oil (4.9 g, 91% purity, 93%).

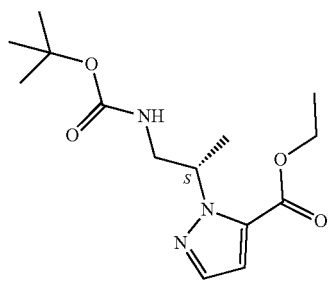

Intermediate 5 (I-5)

Intermediate compound I-5 was synthesized following a similar approach described for intermediate I-4. Starting from intermediate I-1 (25.82 g, 184.25 mmol) and intermediate I-3 (47.16 g, 239.5 mmol), intermediate compound I-5 was obtained as a yellow oil (123 g, quant) which was used in the following step without further purification.

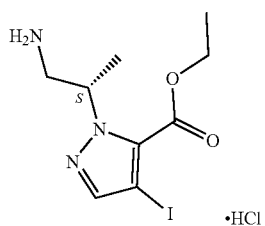

Intermediate 6 (I-6)

A 4M solution of HCl in 1,4-dioxane (10 mL, 40 mmol) was added to a solution of intermediate I-4 (4.2 g, 9.63 mmol) in acetonitrile (20 mL). The mixture was stirred at 80° C. for 2 h. The solvent was evaporated in vacuo to yield intermediate compound I-6 (3.5 g, 97%).

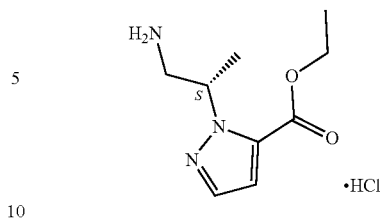

Intermediate 7 (I-7)

Intermediate compound I-7 was synthesized following a similar approach described for intermediate I-6. Starting from intermediate I-5 (54.79 g, 184.25 mmol) and a 4M solution of HCl in 1,4-dioxane (415 mL, 1.66 mol), intermediate compound I-7 was obtained as a white solid (32.5 g, 82% purity, 75%) which was used in the following step without further purification.

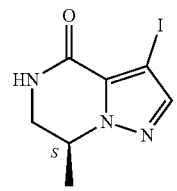

Intermediate 8 (I-8)

Intermediate 1-6 as HCl salt (180 g, 350.4 mmol) was dissolved in a sat. sol. of $NaHCO_3$ (2 L). The mixture was stirred at rt for 12 h. The mixture was diluted with water and extracted with DCM. The organic layers were separated, dried ($Na_2SO_4$), filtered and the solvents evaporated in vacuo. Then the residue was washed with tert-butyl methyl ether to yield intermediate compound I-8 (92 g, 90%).

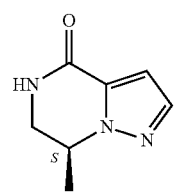

Intermediate 9 (I-9)

Intermediate compound I-9 was synthesized following a similar approach described for intermediate I-8. Starting from intermediate I-7 (32.5 g, 139.1 mmol), intermediate compound I-9 was obtained as a solid (14.8 g, 70%).

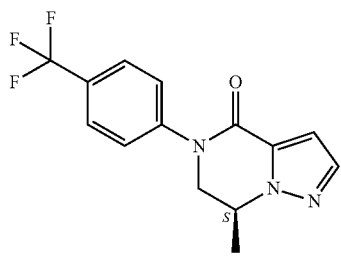

Intermediate 10 (I-10)

A mixture of intermediate I-9 (5 g, 33.01 mmol), copper (I) iodide (3.78 g, 19.85 mmol) and $K_2CO_3$ (9.14 g, 66.15 mmol) in toluene (150 mL) was nitrogen flushed for a few min. Then 4-bromobenzotrifluoride (9.3 mL, 66.1 mmol) and N,N'-dimethylethylenediamine (2.1 mL, 19.8 mmol) were added. The mixture was stirred under nitrogen at rt for 10 min and then stirred at 100° C. for 16 h. Then, DMF (20 mL) was added and the mixture was stirred at 100° C. for 8 h. Then water, a conc. sol. of ammonia and DCM were added. The organic layer was separated, dried (Na$_2$SO$_4$), filtered and the solvents evaporated in vacuo. The crude product was purified by flash column chromatography (silica; EtOAc in DCM 0/100 to 50/50). The desired fractions were collected and the solvents evaporated in vacuo to yield intermediate compound I-14 as a pale yellow oil (9.6 g, 98%).

In a procedure analogous to that described for intermediate I-10, the following intermediates were synthesized:

| Starting Material | Reagent | Intermediate Product |
|---|---|---|
| I-9 | 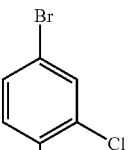<br>(solvent: toluene/DMF) | 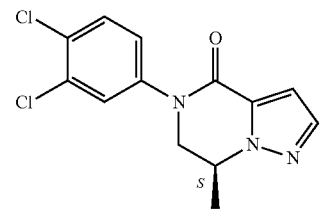<br>I-11 |
| I-9 | 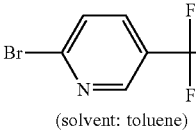<br>(solvent: toluene) | 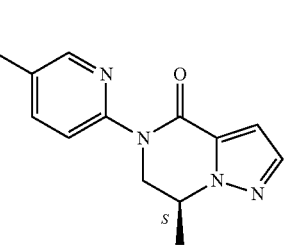<br>I-12(*) |
| I-9 | 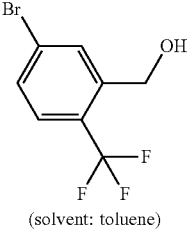<br>(solvent: toluene) | 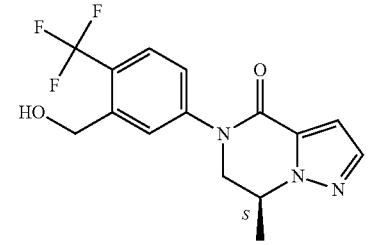<br>I-13 |
| I-9 | 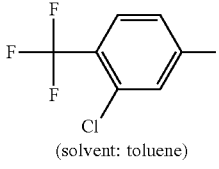<br>(solvent: toluene) | 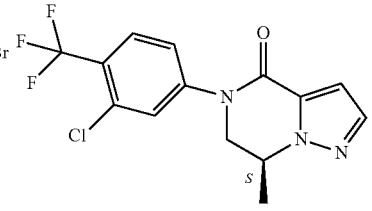<br>I-14 |

(*) Intermediate I-12 was also made according to the following procedure:

Pd(PPh$_3$)$_4$ (764 mg, 0.662 mmol) was added to a stirred suspension of intermediate I-9 (1 g, 6.615 mmol), 2-chloro-5-(trifluoromethyl)pyridine (1.801 g, 9.923 mmol), XantPhos (765 mg, 1.323 mmol), Cs$_2$CO$_3$ (4.311 g, 13.23 mmol) in 1,4-dioxane (30 mL) in a sealed tube and under nitrogen. The mixture was stirred at 90° C. for 40 h. Then the mixture was diluted with water and extracted with DCM. The organic layer was separated, dried (MgSO$_4$), filtered and the solvents evaporated in vacuo. The crude product was purified by flash column chromatography (silica; EtOAc in heptane 0/100 to 75/25). The desired fractions were collected and the solvents concentrated in vacuo to yield intermediate compound I-12 (2.15 g, quant.) as a solid.

In a procedure analogous to that described for intermediate I-12*, the following intermediate were synthesized

| Starting Material | Reagent | Intermediate Product |
|---|---|---|
| I-9 | I-27 | I-28 |
| I-9 | (dichloro trifluoromethyl pyridine) | I-33 |
| I-9 | (methoxy chloro trifluoromethyl pyridine) | I-35 |

Intermediate 15 (I-15)

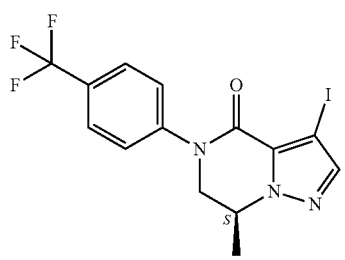

Iodine (11.55 g, 45.5 mmol) was added to a solution of intermediate I-10 (19.2 g, 65.0 mmol) and ammonium cerium(IV) nitrate (24.95 g, 45.5 mmol) in MeCN (350 mL). The mixture was stirred at 70° C. for 1 h. Then the mixture was diluted with EtOAc and washed with a sat. sol. of $Na_2S_2O_3$ and brine. The organic layer was separated, dried ($Na_2SO_4$), filtered and the solvents evaporated in vacuo. The residue was precipitated with DIPE and then was purified by short column chromatography (silica, DCM) then by flash column chromatography (silica; DCM in Heptane 50/50 to 100/0). The desired fractions were collected and the solvents evaporated in vacuo to yield intermediate compound I-15 as a solid (24.8 g, 90%).

In a procedure analogous to that described for intermediate I-15, the following intermediates were synthesized:

| Starting Material | Intermediate obtained |
|---|---|
| I-11 | I-16 |
| I-12 | I-17 |

| Starting Material | Intermediate obtained |
|---|---|
| I-13 | 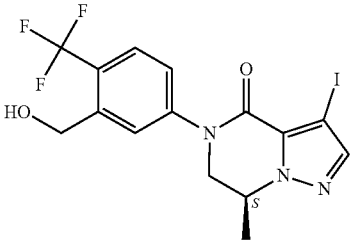 I-18 |
| I-14 | 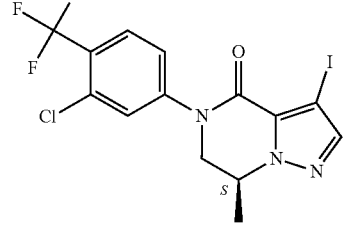 I-19 |
| I-28 | 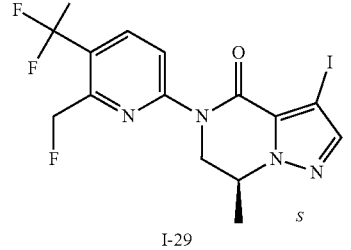 I-29 |
| I-33 | 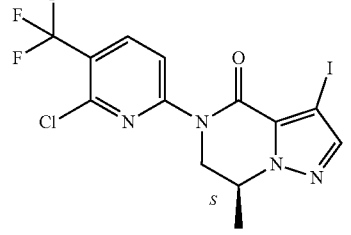 I-34 |
| I-35 | 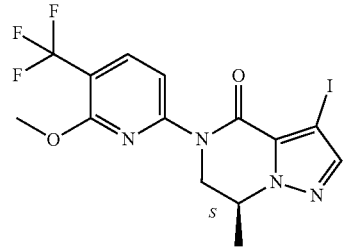 I-36 |

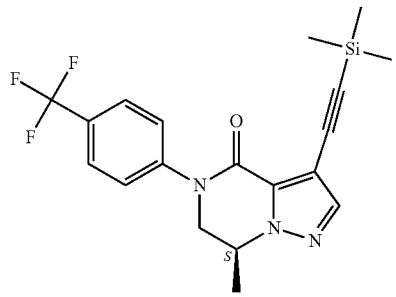

Intermediate 20 (I-20)

PdCl$_2$(PPh$_3$)$_2$ (50 mg, 0.071 mmol) was added to a stirred solution of intermediate I-15 (1 g, 2.37 mmol), trimethylsilylacetylene (0.68 mL, 4.75 mmol), copper(I) iodide (5 mg, 0.02 mmol) and Et$_3$N (0.99 mL, 7.12 mmol) in degassed DMF (10 mL). The mixture was stirred at 55° C. for 1.5 h and at rt for 1 h. Then water, a concentrated sol. of ammonia and EtOAc were added. The organic layer was separated, dried (Na$_2$SO$_4$), filtered and the solvents evaporated in vacuo. The crude product was purified by flash column chromatography (silica; EtOAc in Heptane 0/100 to 50/50). The desired fractions were collected and the solvents evaporated in vacuo to yield intermediate compound I-20 as a brown solid (0.97 g, quant.).

In a procedure analogous to that described for intermediate I-20, the following intermediate was synthesized:

| Starting Material | Intermediate obtained |
|---|---|
| I-16 | 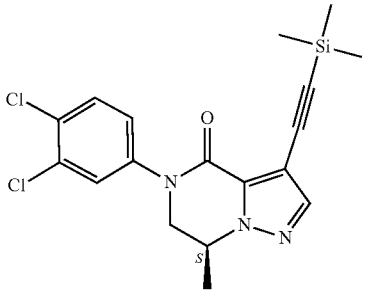 I-21 |
| I-19 | 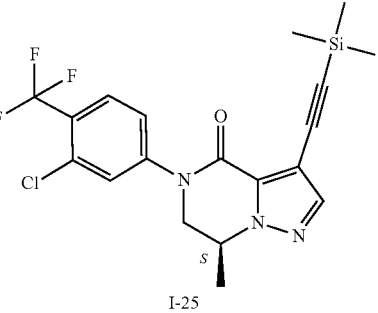 I-25 |

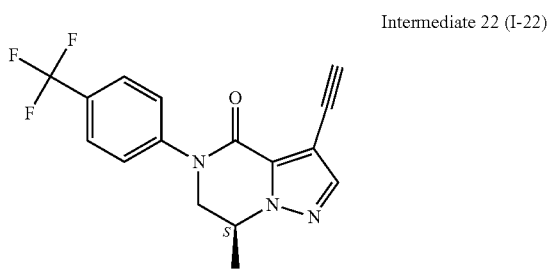

Intermediate 22 (I-22)

K$_2$CO$_3$ (171 mg, 1.24 mmol) was added to a stirred solution of intermediate I-15 (0.97 g, 2.48 mmol) in MeOH (10 mL) at rt and under nitrogen. The mixture was stirred at rt for 2 h. The solvent was removed in vacuo and the residue was diluted with water and extracted with EtOAc. The organic layer was separated, dried (Na$_2$SO$_4$), filtered and the solvents evaporated in vacuo. The crude product was purified by flash column chromatography (silica; EtOAc in DCM 0/100 to 30/70). The desired fractions were collected and the solvents evaporated in vacuo to yield intermediate compound I-22 as a beige solid (549 mg, 69%).

In a procedure analogous to that described for intermediate I-22, the following intermediate was synthesized:

| Starting Material | Intermediate obtained |
|---|---|
| I-21 | I-23 |
| I-25 | I-26 |

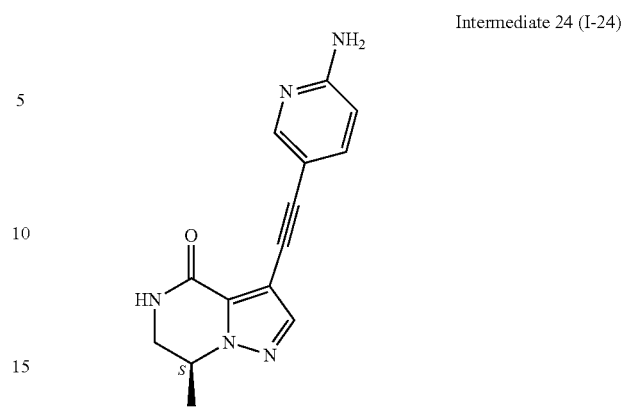

Intermediate 24 (I-24)

Copper(I) iodide (6.279 mg, 0.033 mmol) was added to a stirred mixture of intermediate I-8 (913 mg, 3.297 mmol), 5-ethynyl-2-pyridinamine (779 mg, 6.594 mmol), Et$_3$N (1.4 mL, 9.891 mmol), PdCl$_2$(PPh$_3$)$_2$ (46 mg, 0.0659 mmol) and PPh$_3$ (17.295 mg, 0.0659 mmol) in DMF (7.659 mL). The mixture was purged with nitrogen for 5 min and then it was stirred at 90° C. for 16 h. The mixture was diluted with water and extracted with EtOAc. The organic layer was separated, dried (Na$_2$SO$_4$), filtered and the solvents concentrated in vacuo. The crude product was purified by flash column chromatography (silica; MeOH in DCM 0/100 to 6/94). The desired fractions were collected and the solvents concentrated in vacuo. The residue was precipitated with DIPE and filtered to yield intermediate compound I-24 (581 mg, 66%) as a yellow solid.

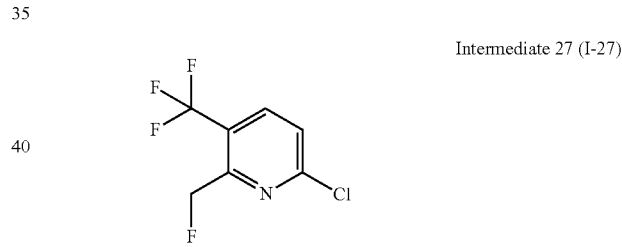

Intermediate 27 (I-27)

Diethylaminosulfur trifluoride (0.533 mL; 4.35 mmol) was added dropwise to a stirred solution of 6-chloro-3-(trifluoromethyl)-pyridinemethanol [1564493-51-1] (0.307 g; 1.45 mmol) in DCM (17.3 mL) at 0° C. and under N$_2$. The mixture was left to warm up to room temperature and stirred for 2 hours. The mixture was carefully treated with sat. NaHCO$_3$ at 0° C. and extracted with diethyl ether. The organic layer was separated, dried (Na$_2$SO$_4$), filtered and evaporated in vacuo (at 25° C. and 300 mbar) to yield intermediate compound I-27 (0.392 g; 72%) as a brown oil which was used without further purification.

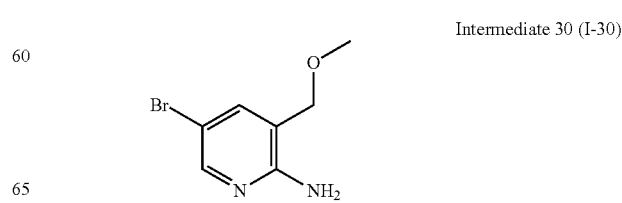

Intermediate 30 (I-30)

Sodium hydride (75.486 mg; 1.97 mmol) was added to a stirred solution of 2-amino-5-bromo-3-pyridinemethanol (200 mg; 0.985 mmol) in THF (14 ml) at 0° C. The mixture was stirred at room temperature for 15 minutes and CH$_3$I (122.645 µl; 1.97 mmol) was added. The mixture was stirred at room temperature for 1.5 hours. The mixture was treated with water and extracted with ethyl acetate. The organic layer was separated, dried (Na$_2$SO$_4$), filtered and concentrated in vacuo. The crude product was purified by flash column chromatography (silica; ethyl acetate in DCM 0/100 to 30/70). The desired fractions were collected and evaporated in vacuo to yield intermediate compound I-30 (74.1 mg; 35%).

In a procedure analogous to that described for intermediate I-30, the following intermediate was synthesized:

| Starting Material | Intermediate obtained |
|---|---|
| 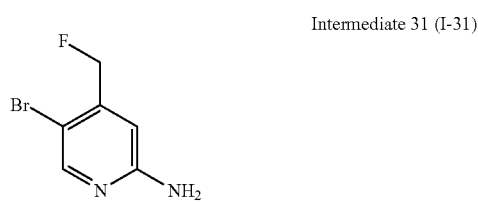 | |

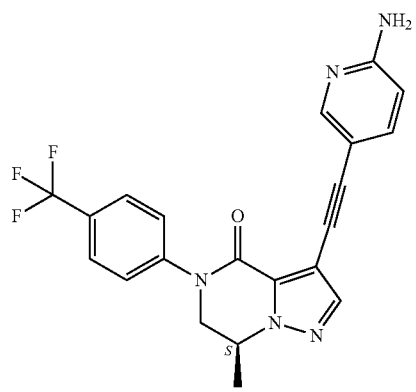

Intermediate 31 (I-31)

CXtalfluor-E (0.338 g; 1.478 mmol) and trimethylamine trihydrofluoride (0.241 mL; 1.478 mmol) were added to a stirred mixture of 2-amino-5-bromo-4-pyridinemethanol (0.2 g; 0.985 mmol) in DCM (14 mL) in a sealed tube at 0° C. and under nitrogen. The mixture was allowed to warm and stirred for 18 hours. The mixture was carefully treated with sat. NaHCO$_3$/brine at 0° C. and extracted with DCM. The organic layer was separated, dried (Na$_2$SO$_4$), filtered and evaporated in vacuo. The residue was purified by flash column chromatography (silica; ethyl acetate in DCM 0/100 to 30/70). The desired fractions were collected and concentrated in vacuo to yield intermediate compound I-31 (94.4 mg; 47%) as a beige solid.

Preparation of Final Compounds

Example 1 (E-1)

(7S)-3-[2-(6-Amino-3-pyridyl)ethynyl]-7-methyl-5-[4-(trifluoromethyl)phenyl]-6,7-dihydropyrazolo[1,5-a]pyrazin-4-one (Co. No. 1)

Copper (I) iodide (1.131 mg, 5 µmol) was added to a stirred mixture of intermediate I-15 (250 mg, 0.594 mmol), 5-ethynyl-2-pyridinamine (140 mg, 1.187 mmol), Et$_3$N (248 µL, 1.781 mmol), PdCl$_2$(PPh$_3$)$_2$ (8 mg, 0.012 mmol) and PPh$_3$ (3 mg, 0.0119 mmol) in DMF (1.4 mL). The mixture was purged with nitrogen for 5 min and then it was stirred at 90° C. for 5 h. The mixture was diluted with water and extracted with EtOAc. The organic layer was separated, dried (Na$_2$SO$_4$), filtered and the solvents concentrated in vacuo. The crude product was purified by flash column chromatography (silica; MeOH in DCM 0/100 to 6/94). The desired fractions were collected and the solvents concentrated in vacuo. The solid was precipitated with DIPE/Heptane then DIPE and filtered to yield final compound Co. No. 1 (190 mg, 78%) as a pale yellow solid. $^1$H NMR (400 MHz, CDCl$_3$) δ ppm 1.70 (d, J=6.5 Hz, 3H) 3.97 (dd, J=12.6, 7.3 Hz, 1H) 4.24 (dd, J=12.7, 4.2 Hz, 1H) 4.58 (br. s, 2H) 4.73 (quind, J=6.7, 4.3 Hz, 1H) 6.43 (dd, J=8.6, 0.7 Hz, 1H) 7.52 (d, J=8.3 Hz, 2H) 7.57 (dd, J=8.6, 2.1 Hz, 1H) 7.70 (d, J=8.6 Hz, 2H) 7.74 (s, 1H) 8.27 (d, J=1.6 Hz, 1H).

Following a procedure analogous to that described for E-1, the following compounds were also synthesized:

| Starting material | Reagent | Intermediate product |
|---|---|---|
| I-16 | 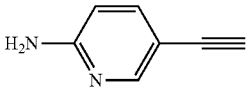 | 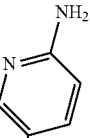<br>Co. No. 2(**) |
| I-23 | 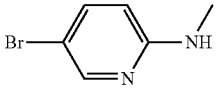 | 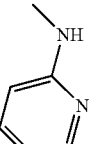<br>Co. No. 3 |
| I-16 | 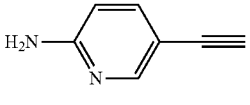 | 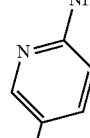<br>Co. No. 4 |
| I-15 | 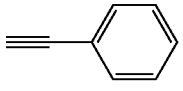 | 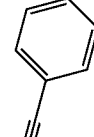<br>Co. No. 5 |

| Starting material | Reagent | Intermediate product |
|---|---|---|
| I-23 | 5-bromo-2-methoxypyridine | Co. No. 6 |
| I-23 | 5-bromo-2-fluoropyridine | Co. No. 7 |
| I-22 | 4-bromo-2-methylpyridine | Co. No. 9 |
| I-22 | 4-bromo-2-aminopyridine | Co. No. 10 |

-continued
| Starting material | Reagent | Intermediate product |
|---|---|---|
| I-22 | 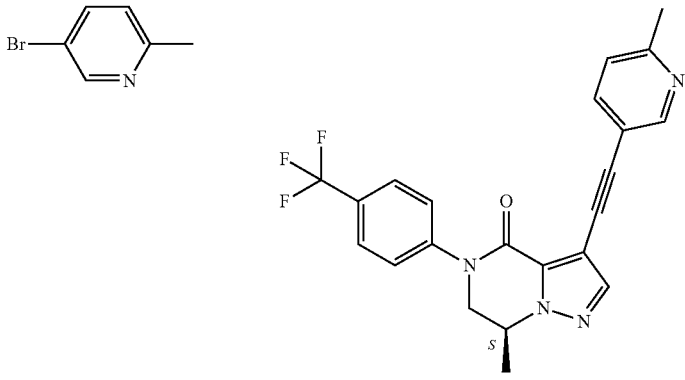 | Co. No. 11 |
| I-19 | 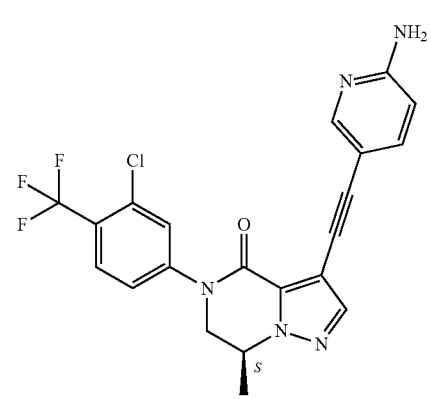 | Co. No. 13 |
| I-18 | 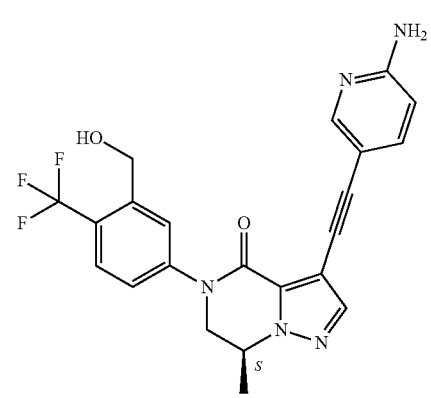 | Co. No. 14 |
| I-15 | 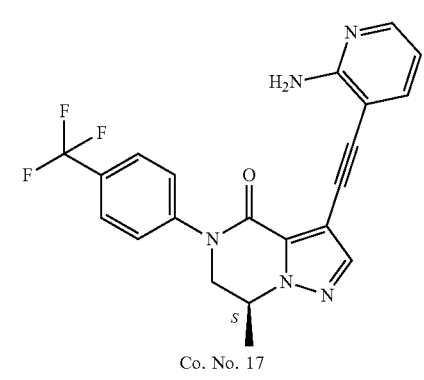 | Co. No. 17 |

-continued
| Starting material | Reagent | Intermediate product |
|---|---|---|
| I-29 | 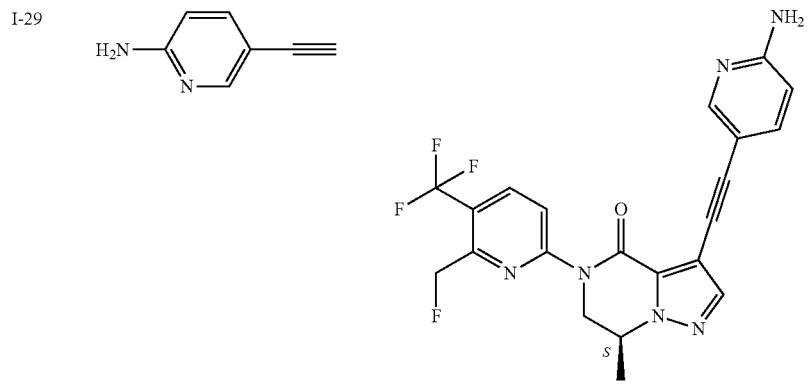 | <br>Co. No. 19 |
| I-22 | I-30 | 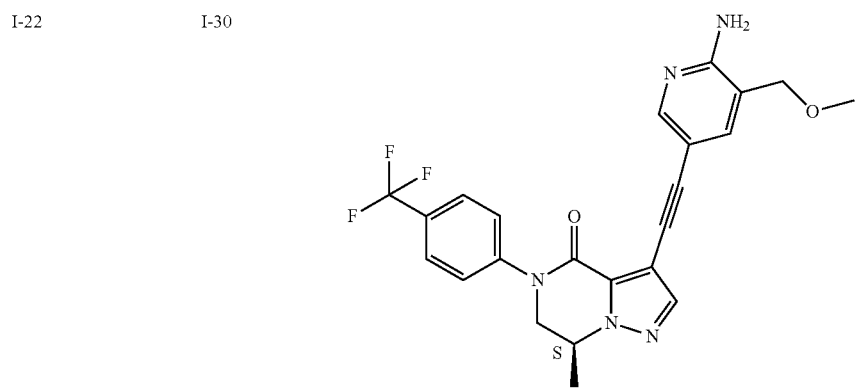<br>Co. No. 20 |
| I-22 | 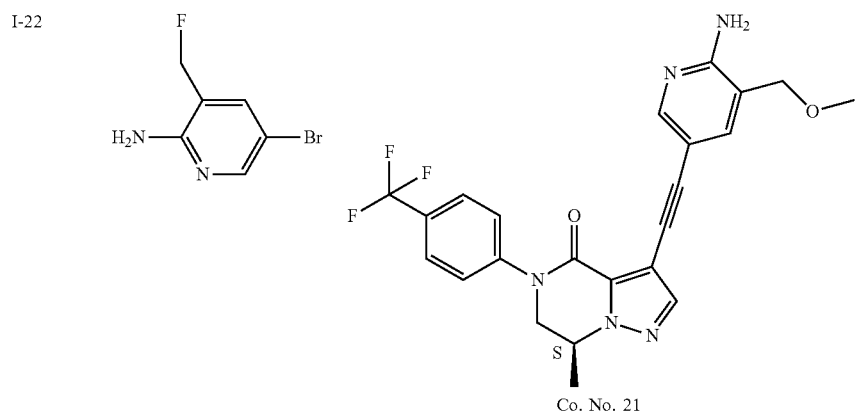 | <br>Co. No. 21 |

-continued

| Starting material | Reagent | Intermediate product |
|---|---|---|
| I-26 | 5-bromo-2-amino-4-(hydroxymethyl)pyridine | Co. No. 22 |
| I-22 | I-31 | Co. No. 3 |
| I-22 | 3-iodo-2-(methylamino)pyridine | Co. No. 24 |
| I-22 | I-32 | Co. No. 25 |

| Starting material | Reagent | Intermediate product |
|---|---|---|
| I-22 | 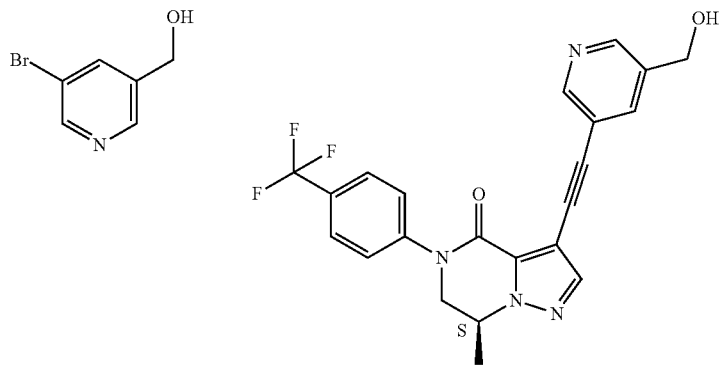 | Co. No. 28 |
| I-22 | 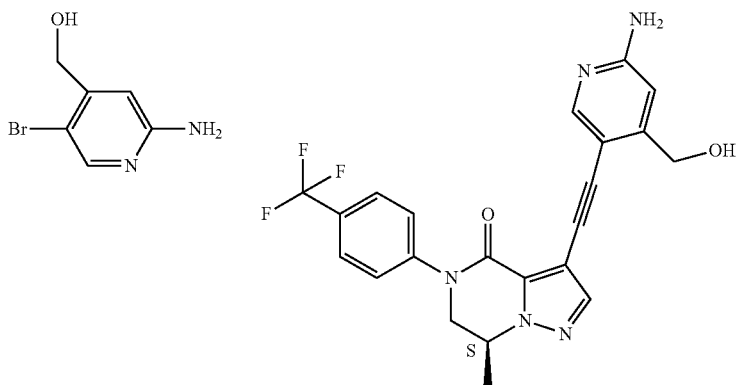 | Co. No. 29 |
| I-22 | 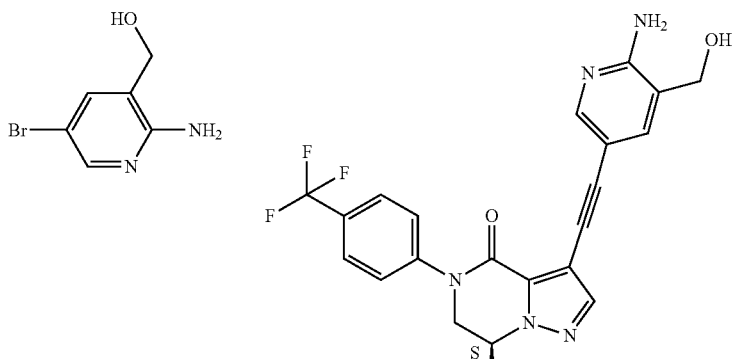 | Co. No. 30 |

-continued
| Starting material | Reagent | Intermediate product |
|---|---|---|
| I-34 | 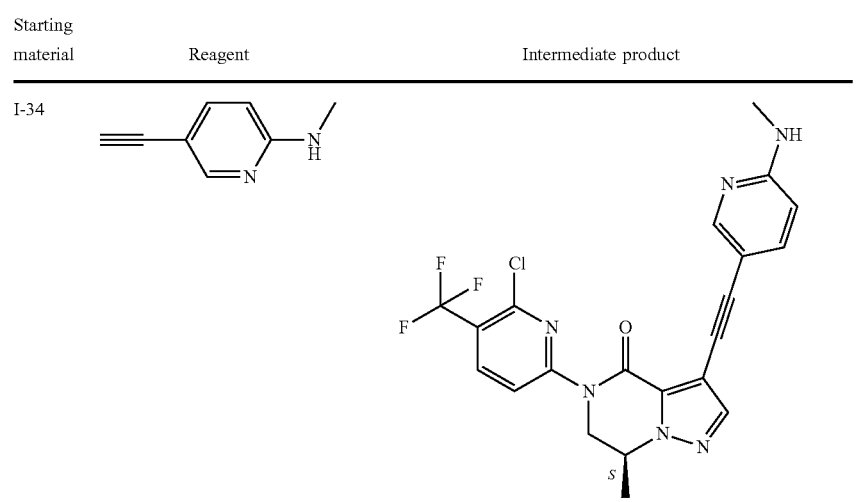 | |
| | | Co. No. 31 |
| I-36 | 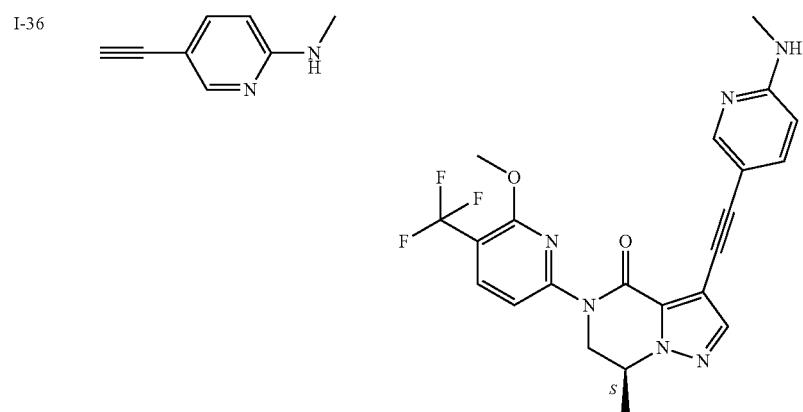 | |
| | | Co. No. 32 |
| I-36 | 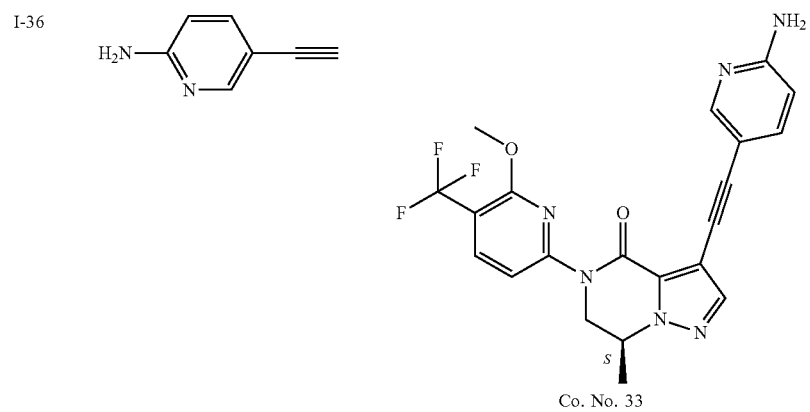 | |
| | | Co. No. 33 |

-continued

| Starting material | Reagent | Intermediate product |
|---|---|---|
| I-22 | 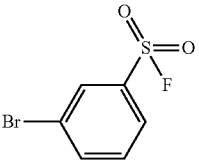 | 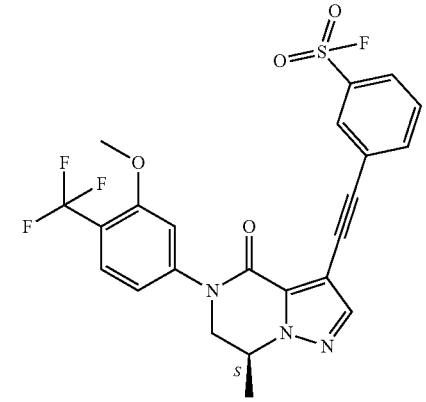  Co. No. 34 |
| I-22 | 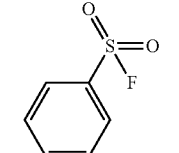 | 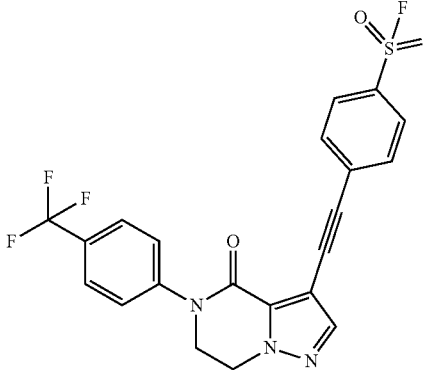  Co. No. 35 |

(**)Alternatively, compound Co. No. 2 was also synthesized according to a procedure analogous to that described for the synthesis of compound Co. No. 8 below:

Example 2 (E-2)

(7S)-3-[2-(6-Amino-3-pyridyl)ethynyl]-5-(3-chloro-4-methoxy-phenyl)-7-methyl-6,7-dihydropyrazolo[1,5-a]pyrazin-4-one (Co. No. 8)

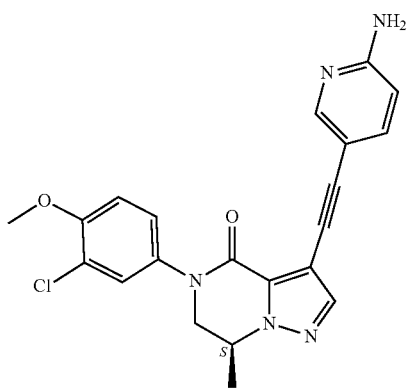

Copper(I) iodide (64 mg, 0.337 mmol) was added to a stirred suspension of intermediate I-24 (150 mg, 0.561 mmol), 4-bromo-2-chloro-1-methoxy-benzene (199 mg, 0.898 mmol), $K_2CO_3$ (155 mg, 1.122 mmol) and N,N'-dimethylethylenediamine (36 µL, 0.337 mmol) in toluene (3.6 mL) in a sealed tube and under nitrogen. The mixture was stirred at 100° C. for 20 h. Then additional copper(I) iodide (43 mg, 0.224 mmol) was added and the resulting mixture was stirred at 100° C. for 16 h. Then, additional N,N'-dimethylethylenediamine (24 µL, 0.224 mmol) and DMF (0.5 mL) were added and the mixture was stirred at 100° C. for 6 h. The mixture was filtered through a pad of diatomaceous earth and washed with DCM. The filtrate was evaporated in vacuo. The crude product was purified by flash column chromatography (silica; 7N solution of ammonia in MeOH in DCM 0/100 to 3/97). The desired fractions were collected and the solvents concentrated in vacuo to yield final compound Co. No. 8 (60 mg, 26%) as a yellow solid. $^1$H NMR (500 MHz, $CDCl_3$) δ ppm 1.68 (d, J=6.6 Hz, 3H) 3.86 (dd, J=12.9, 7.1 Hz, 1H) 3.92 (s, 3H) 4.16 (dd, J=12.9, 4.2 Hz, 1H) 4.57 (br. s., 2H) 4.65-4.73 (m, 1H) 6.42 (d, J=8.4 Hz, 1H) 6.97 (d, J=9.0 Hz, 1H) 7.20-7.30 (m, 1H) 7.39 (d, J=2.6 Hz, 1H) 7.56 (dd, J=8.5, 2.2 Hz, 1H) 7.73 (s, 1H) 8.27 (d, J=1.7 Hz, 1H).

Following a procedure analogous to that described for E-2, the following compound was also synthesized:

| Starting Material | Reagent | Final Compound |
|---|---|---|
| I-24 | | 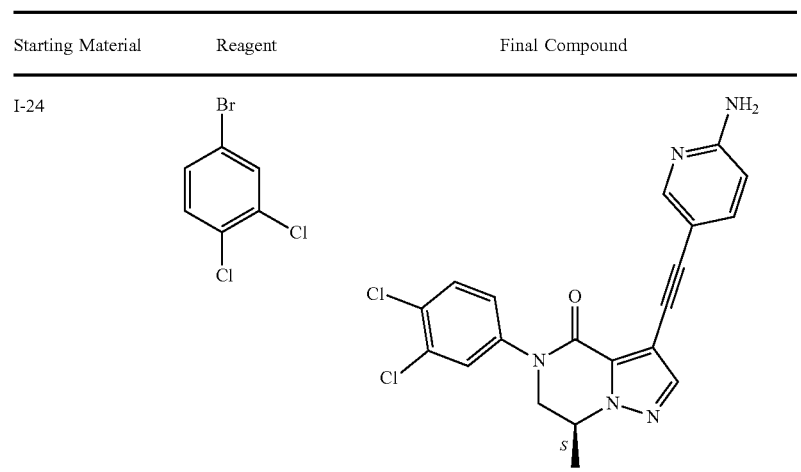 |
| | | Co. No. 2 |
| I-24 | | 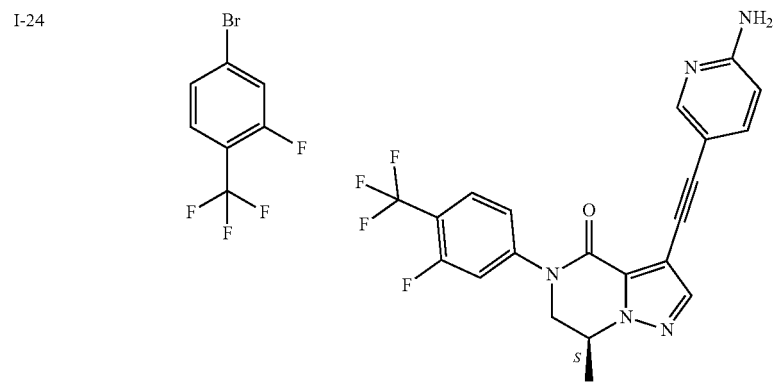 |
| | | Co. No. 18 |
| I-24 | | 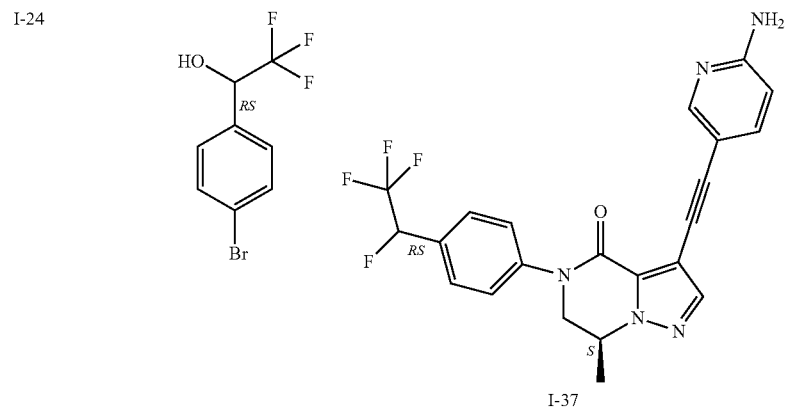 |
| | | I-37 |

Example 3 (E-3)

(7S)-5-(3,4-Dichlorophenyl)-3-[2-[6-(dimethyl-amino)-3-pyridyl]ethynyl]-7-methyl-6,7-dihydropyrazolo[1,5-a]pyrazin-4-one (Co. No. 12)

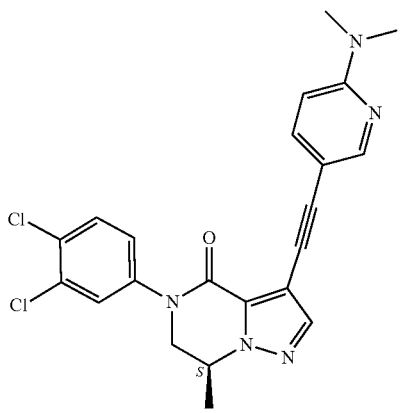

A mixture of compound Co. No. 7 (50 mg, 0.12 mmol) and diethylamine (0.903 mL, 1.806 mmol) in EtOH (1 mL) in a sealed tube was stirred at 130° C. for 15 min under microwave irradiation. The mixture was diluted with EtOAc and washed with a sat. sol. of NaHCO$_3$ and with water. The organic layer was dried (MgSO$_4$), filtered and the solvents evaporated in vacuo. The crude product was purified by flash column chromatography (silica; EtOAc in DCM 0/100 to 50/50). The desired fractions were collected and the solvents concentrated in vacuo to yield final compound Co. No. 12 (43 mg, 81%) as a yellow solid. $^1$H NMR (400 MHz, CDCl$_3$) δ ppm 1.68 (d, J=6.7 Hz, 3H) 3.10 (s, 6H) 3.89 (dd, J=12.6, 7.3 Hz, 1H) 4.18 (dd, J=12.5, 4.2 Hz, 1H) 4.70 (quind, J=6.7, 4.3 Hz, 1H) 6.43 (dd, J=8.8, 0.7 Hz, 1H) 7.23-7.27 (m, 1H) 7.50 (d, J=8.6 Hz, 1H) 7.52 (d, J=2.5 Hz, 1H) 7.57 (dd, J=8.8, 2.3 Hz, 1H) 7.73 (s, 1H) 8.34 (dd, J=2.3, 0.7 Hz, 1H).

Example 4 (E-4) (Co. No. 15)

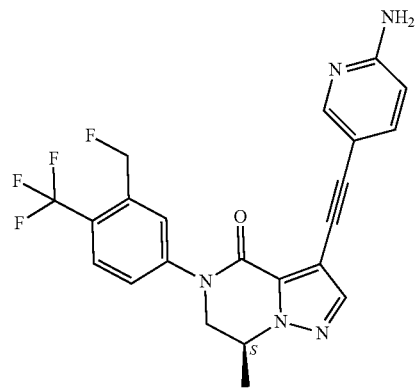

Bis(2-methoxyethyl)amino-sulfur trifluoride (0.915 mL, 4.961 mmol) was added to a stirred solution of compound Co. No. 14 (438 mg, 0.992 mmol) in DCM (6.2 mL) at 0° C. and under nitrogen. The mixture was stirred at 0° C. for 45 min. Then the mixture was treated with sat. sol. NaHCO$_3$ at 0° C. and extracted with DCM and EtOAc. The organic layer was separated, dried (Na$_2$SO$_4$), filtered and the solvents concentrated in vacuo. The crude product was purified by flash column chromatography (silica; EtOAc in DCM 0/100 to 50/50). The desired fractions were collected and the solvents concentrated in vacuo. The residue was triturated with Et$_2$O to yield an impure fraction as a yellow solid and was purified by RP HPLC (Stationary phase: C18 XBridge 50×100 5 μm, Mobile phase: Gradient from 80% 10 mM NH$_4$CO$_3$H pH 9 solution in Water, 20% MeCN to 0% 10 mM NH$_4$CO$_3$H pH 9 solution in Water, 100% MeCN) to yield final compound Co. No. 15 (55 mg, 12%) as a pale yellow solid. $^1$H NMR (400 MHz, CDCl$_3$) δ ppm 1.71 (d, J=6.5 Hz, 3H) 3.99 (dd, J=12.7, 7.4 Hz, 1H) 4.26 (dd, J=12.5, 4.2 Hz, 1H) 4.59 (br. s, 2H) 4.74 (quind, J=6.7, 4.4 Hz, 1H) 5.63 (d, J=46.7 Hz, 2H) 6.43 (dd, J=8.6, 0.7 Hz, 1H) 7.52 (dd, J=8.4, 0.8 Hz, 1H) 7.57 (dd, J=8.6, 2.3 Hz, 1H) 7.67 (s, 1H) 7.72-7.76 (m, 2H) 8.27 (dd, J=2.2, 0.6 Hz, 1H).

Following a procedure analogous to that described for E-4, the following compound was also synthesized:

| Starting Material | Reagent | Final Compound |
|---|---|---|
| I-37 prepared according to E-2 | ![reagent] | Co. No. 16* |

| Starting Material | Reagent | Final Compound |
|---|---|---|
| Co. No. 28 prepared according to E-1 | XtalFluor-E | 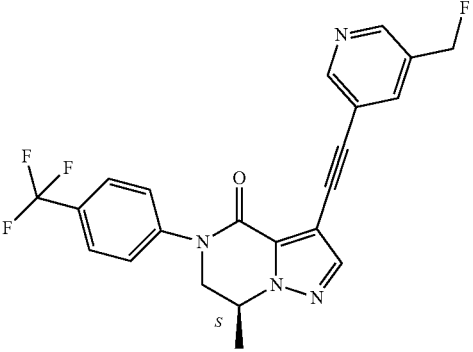 Co. No. 26* |

*The mixture was stirred at −78° C. to 0° C. in 4 h instead of at 0° C. for 45 min.

Example 5 (E-5) (Co. No. 27)

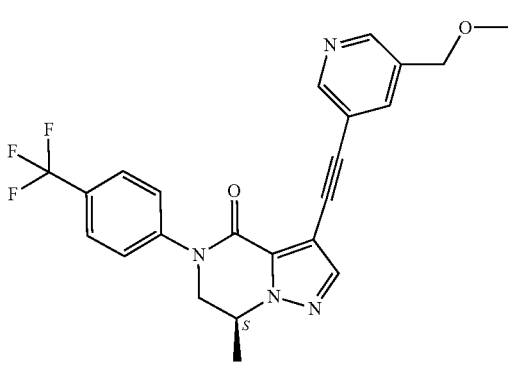

Sodium hydride (12.365 mg; 0.323 mmol) was added to a stirred solution of Co. No. 28 (prepared according to E-1) (68.8 mg; 0.161 mmol) in THF (4.07 mL) at 0° C. The mixture was stirred at room temperature for 15 minutes and methyliodide (20.09 μL; 0.323 mmol) was added. The mixture was stirred at room temperature for 2 hours. Then more sodium hydride (5.56 mg; 0.145 mmol) and methyliodide (5.02 μL; 0.0807 mmol) were added at 0° C. and the mixture was stirred at room temperature for 18 hours more. The mixture was treated with sat. $NH_4Cl$/brine and extracted with ethyl acetate. The organic layer was separated, dried ($Na_2SO_4$), filtered and concentrated in vacuo. The residue was purified by flash column chromatography (silica; ethyl acetate in $CH_2Cl_2$ 0/100 to 100/0). The desired fractions were collected and concentrated in vacuo. Then the product was triturated with diethyl ether to yield Co. No. 27 (15.9 mg; 22%) as a beige solid.

TABLE 1

The following compounds were prepared following the methods exemplified in the Experimental Part (Ex. No.). Compounds exemplified and described in the experimental part are marked with an asterisk *.

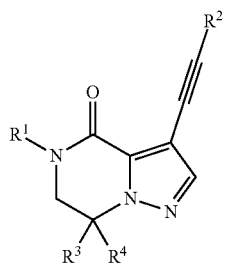

| Co. No. | Exp. No. | $R^1$ | $R^2$ | $>CR^3R^4$ |
|---|---|---|---|---|
| 1 | E-1* | $F_3C$-phenyl | 2-amino-pyridin-5-yl | $>CH(CH_3)$ (S) |

TABLE 1-continued

The following compounds were prepared following the methods exemplified in the Experimental Part (Ex. No.). Compounds exemplified and described in the experimental part are marked with an asterisk *.

| Co. No. | Exp. No. | R¹ | R² | >CR³R⁴ |
|---|---|---|---|---|
| 2 | E-1 | 3,4-dichlorophenyl | 6-amino-pyridin-3-yl | >CH(CH$_3$) (S) |
| 3 | E-1 | 3,4-dichlorophenyl | 6-(methylamino)-pyridin-3-yl | >CH(CH$_3$) (S) |
| 4 | E-1 | 5-(trifluoromethyl)-pyridin-2-yl | 6-amino-pyridin-3-yl | >CH(CH$_3$) (S) |
| 5 | E-1 | 4-(trifluoromethyl)phenyl | phenyl | >CH(CH$_3$) (S) |
| 6 | E-1 | 3,4-dichlorophenyl | 6-methoxy-pyridin-3-yl | >CH(CH$_3$) (S) |
| 7 | E-1 | 3,4-dichlorophenyl | 6-fluoro-pyridin-3-yl | >CH(CH$_3$) (S) |
| 8 | E-1/E-2* | 3-chloro-4-methoxyphenyl | 6-amino-pyridin-3-yl | >CH(CH$_3$) (S) |
| 9 | E-1 | 4-(trifluoromethyl)phenyl | 2-methyl-pyridin-4-yl | >CH(CH$_3$) (S) |

TABLE 1-continued
The following compounds were prepared following the methods exemplified in the Experimental Part (Ex. No.). Compounds exemplified and described in the experimental part are marked with an asterisk *.
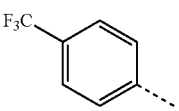
| Co. No. | Exp. No. | R¹ | R² | >CR³R⁴ |
|---|---|---|---|---|
| 10 | E-1 | 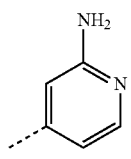 | 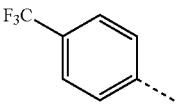 | >CH(CH$_3$) (S) |
| 11 | E-1 | 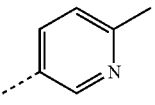 | 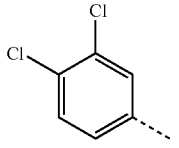 | >CH(CH$_3$) (S) |
| 12 | E-3 | 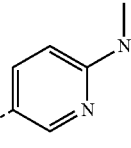 | 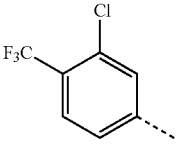 | >CH(CH$_3$) (S) |
| 13 | E-1 | 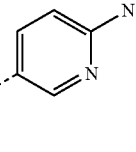 | 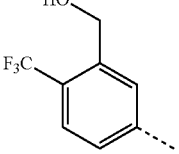 | >CH(CH$_3$) (S) |
| 14 | E-1 | 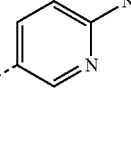 | 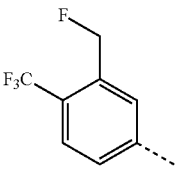 | >CH(CH$_3$) (S) |
| 15 | E-4 | 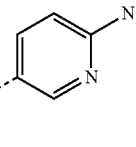 | 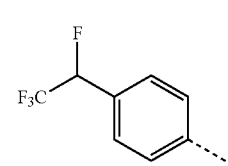 | >CH(CH$_3$) (S) |
| 16 | E-4 | 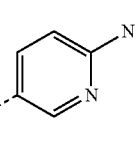 | | >CH(CH$_3$) (S) |

TABLE 1-continued
The following compounds were prepared following the methods exemplified in the Experimental Part (Ex. No.). Compounds exemplified and described in the experimental part are marked with an asterisk *.
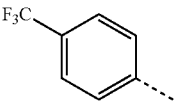
| Co. No. | Exp. No. | R¹ | R² | >CR³R⁴ |
|---|---|---|---|---|
| 17 | E-1 | 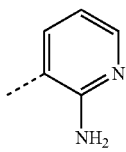 | 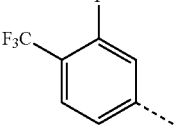 | >CH(CH₃) (S) |
| 18 | E-2 | 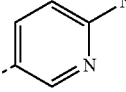 | 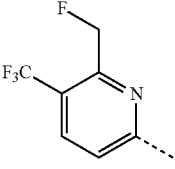 | >CH(CH₃) (S) |
| 19 | E-1 | 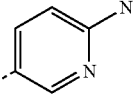 | 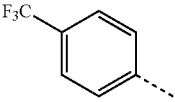 | >CH(CH₃) (S) |
| 20 | E-1 | 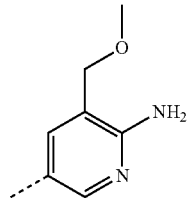 | 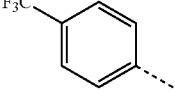 | >CH(CH₃) (S) |
| 21 | E-1 | 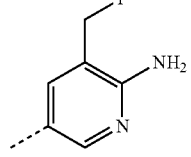 | 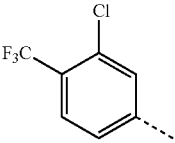 | >CH(CH₃) (S) |
| 22 | E-1 | 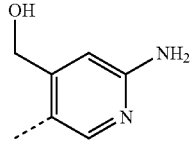 | 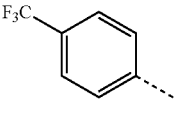 | >CH(CH₃) (S) |
| 23 | E-1 | 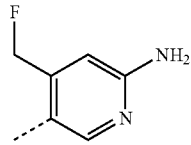 | | >CH(CH₃) (S) |

TABLE 1-continued

The following compounds were prepared following the methods exemplified in the Experimental Part (Ex. No.). Compounds exemplified and described in the experimental part are marked with an asterisk *.

| Co. No. | Exp. No. | $R^1$ | $R^2$ | $>CR^3R^4$ |
|---|---|---|---|---|
| 24 | E-1 | 4-F₃C-phenyl | 2-(methylamino)pyridin-3-yl | $>CH(CH_3)$ (S) |
| 25 | E-1 | 4-F₃C-phenyl | 2-amino-4-(methoxymethyl)pyridin-5-yl | $>CH(CH_3)$ (S) |
| 26 | E-4 | 4-F₃C-phenyl | 5-(fluoromethyl)pyridin-3-yl | $>CH(CH_3)$ (S) |
| 27 | E-5 | 4-F₃C-phenyl | 5-(methoxymethyl)pyridin-3-yl | $>CH(CH_3)$ (S) |
| 28 | E-1 | 4-F₃C-phenyl | 5-(hydroxymethyl)pyridin-3-yl | $>CH(CH_3)$ (S) |
| 29 | E-1 | 4-F₃C-phenyl | 2-amino-4-(hydroxymethyl)pyridin-5-yl | $>CH(CH_3)$ (S) |
| 30 | E-1 | 4-F₃C-phenyl | 2-amino-3-(hydroxymethyl)pyridin-5-yl | $>CH(CH_3)$ (S) |

TABLE 1-continued

The following compounds were prepared following the methods exemplified in the Experimental Part (Ex. No.). Compounds exemplified and described in the experimental part are marked with an asterisk *.

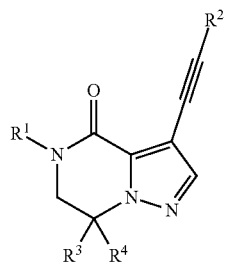

| Co. No. | Exp. No. | $R^1$ | $R^2$ | $>CR^3R^4$ |
|---|---|---|---|---|
| 31 | E-1 | 2-Cl-3-CF$_3$-pyridin-6-yl | 6-(methylamino)pyridin-3-yl | $>CH(CH_3)$ (S) |
| 32 | E-1 | 2-methoxy-3-CF$_3$-pyridin-6-yl | 6-(methylamino)pyridin-3-yl | $>CH(CH_3)$ (S) |
| 33 | E-1 | 2-methoxy-3-CF$_3$-pyridin-6-yl | 6-amino-pyridin-3-yl | $>CH(CH_3)$ (S) |
| 34 | E-1 | 4-CF$_3$-phenyl | 3-fluorosulfonyl-phenyl | $>CH(CH_3)$ (S) |
| 35 | E-1 | 4-CF$_3$-phenyl | 4-fluorosulfonyl-phenyl | $>CH(CH_3)$ (S) |

Analytical Part

Melting Points

Values are peak values, and are obtained with experimental uncertainties that are commonly associated with this analytical method.

Mettler FP 81HT/FP90 Apparatus (A):

For a number of compounds, melting points were determined in open capillary tubes on a Mettler FP 81HT/FP90 apparatus. Melting points were measured with a temperature gradient of 1, 3, 5 or 10° C./min. Maximum temperature was 300° C. The melting point was read from a digital display.

Mettler FP62 Apparatus (B):

For a number of compounds, melting points were determined in open capillary tubes on a Mettler FP62 apparatus. Melting points were measured with a temperature gradient of 1, 3, 5 or 10° C./min. Maximum temperature was 300° C. The melting point was read from a digital display.

DSC823e (C):

For a number of compounds, melting points (m.p.) were determined with a DSC823e (Mettler-Toledo) apparatus. Melting points were measured with a temperature gradient of 10° C./min. Maximum temperature was 300° C. Peak values were recorded.

LCMS

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW) and/or exact mass monoisotopic molecular weight. Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). For molecules with multiple isotopic patterns (Br, Cl.), the reported value is the one obtained for the lowest isotope mass. All results were obtained with experimental uncertainties that are commonly associated with the method used.

TABLE 3

Analytical data - melting point (M.p.) and LCMS: $[M + H]^+$ means the protonated mass of the free base of the compound, $R_t$ means retention time (in min), method refers to the method used for LCMS. For some compounds, exact mass was determined.

| Co. No. | M.p. (° C.) | $[M + H]^+$ | $R_t$ | LCMS Method |
|---|---|---|---|---|
| 1 | >300 (A) | 412 | 2.13 | 1 |
| 2 | 201.6 (A) | 412 | 2.12 | 2 |
| 3 | n.d. | 426 | 3.71 | 3 |
| 4 | 176.9 (A) | 413 | 2.13 | 2 |
| 5 | n.d. | 396 | 2.83 | 2 |
| 6 | 241.8 (B) | 427 | 4.11 | 3 |
| 7 | 202.7 (B) | 415 | 2.64 | 2 |
| 8 | 200.7 (B) | 408 | 1.83 | 2 |
| 9 | 157.4 (A) | 411 | 2.41 | 2 |
| 10 | 179.3 (A) | 412 | 2.08 | 2 |
| 11 | 87.7 (A) | 411 | 2.39 | 2 |
| 12 | 125.9 (B) | 440 | 2.75 | 2 |
| 13 | 206.73 (C) | 446.0998 (+0.3 mDa) | 2.37 | 4 |
| 14 | n.d. | 442 | 1.18 | 5 |
| 15 | n.d. | 444.1454 (+0.7 mDa) | 1.95 | 4 |
| 16 | n.d. | 444.1450 (+0.3 mDa) | 2.18 | 4 |
| 17 | n.d. | 412.1386 (+0.1 mDa) | 2.41 | 6 |
| 18 | 179.97 (C) | 430.1288 (−0.3 mDa) | 2.23 | 4 |

TABLE 2

LC-MS Methods (Flow expressed in mL/min; column temperature (T) in ° C.; Run time in min).

| Method | Instrument | Column | Mobile phase | Gradient | Flow Col T | Run time |
|---|---|---|---|---|---|---|
| 1 | Waters: Acquity ® UPLC ® - DAD and SQD | Agilent: Eclipse Plus C18 RRHD (1.8 µm, 2.1 × 50 mm) | A: 95% CH$_3$COONH$_4$ 6.5 mM + 5% CH$_3$CN, B: CH$_3$CN | From 95% A to 5% A in 4.6 min, held for 0.4 min | 1 50 | 5 |
| 2 | Waters: Acquity ® UPLC ® - DAD/SQD | Waters: CSH ™ C18 (1.7 µm, 2.1 × 50 mm) | A: 95% CH$_3$COONH$_4$ 6.5 mM + 5% CH$_3$CN, B: CH$_3$CN | From 95% A to 5% A in 4.6 min, held for 0.4 min | 1 50 | 5 |
| 3 | Agilent: HP1100-DAD, Waters: SQD | Agilent: Eclipse Plus C18 (3.5 µm, 2.1 × 30 mm) | A: 95% CH$_3$COONH$_4$ 6.5 mM + 5% CH$_3$CN, B: CH$_3$CN/CH$_3$OH, 1/1 | From 95% A to 0% A in 5.0 min, held for 0.15 min, back to 95% A in 0.15 min, held for 1.7 min | 1 60 | 7 |
| 4 | Waters: Acquity ® IClass UPLC ® - DAD/Xevo G2-S QTOF | Waters: CSH ™ C18 (1.7 µm, 2.1 × 50 mm) | A: 95% CH3COONH4 6.5 mM + 5% CH3CN, B: CH3CN | From 95% A to 5% A in 4.6 min, held for 0.4 min | 1 50 | 5 |
| 5 | Waters: Acquity ® IClass UPLC ® - DAD and SQD | Waters: CSH ™ C18 (1.7 µm, 2.1 × 50 mm) | A: 95% CH$_3$COONH$_4$ 6.5 mM + 5% CH$_3$CN, B: CH$_3$CN | From 95% A to 40% A in 1.2 min, to 5% A in 0.6 min, held for 0.2 min | 1 50 | 2 |
| 6 | Waters: Acquity ® IClass UPLC ® - DAD/Xevo G2-S QTOF | Waters: CSH ™ C18 (1.7 µm, 2.1 × 50 mm) | A: 95% CH$_3$COONH$_4$ 6.5 mM + 5% CH$_3$CN, B: CH$_3$CN | From 95% A to 5% A in 4.6 min, held for 0.4 min | 1 50 | 5 |
| 7* | Waters: Acquity ® IClass UPLC ® - DAD/Xevo G2-S QTOF | Waters: CSH ™ C18 (1.7 µm, 2.1 × 50 mm) | A: 95% CH$_3$COONH$_4$ 6.5 mM + 5% CH$_3$CN, B: CH$_3$CN | From 95% A to 5% A in 4.6 min, held for 0.4 min | 1 50 | 5 |

*Different MS tuning parameters

TABLE 3-continued

Analytical data - melting point (M.p.) and LCMS: [M + H]+ means the protonated mass of the free base of the compound, $R_t$ means retention time (in min), method refers to the method used for LCMS. For some compounds, exact mass was determined.

| Co. No. | M.p. (° C.) | [M + H]+ | $R_t$ | LCMS Method |
|---|---|---|---|---|
| 19 | 180.22 (C) | 445.1401 (+0.1 mDa) | 2.33 | 4 |
| 20 | 164.52 (C) | 456.1655 (+0.8 mDa) | 2.30 | 4 |
| 21 | 191.01 (C) (*) | 444.1451 (+0.4 mDa) | 2.28 | 4 |
| 22 | 219.22 (C) | 476.1102 (+0.1 mDa) | 2.14 | 4 |
| 23 | 187.28 (C) (*) | 444.1451 (+0.4 mDa) | 2.29 | 7 |
| 24 | 258.96 (C) | 426.1543 (+0.2 mDa) | 2.80 | 6 |
| 25 | 179.66 (C) | 456.1649 (+0.2 mDa) | 2.25 | 4 |
| 26 | 160.70 (C) | 429.1342 (+0.4 mDa) | 2.44 | 4 |
| 27 | 170.41 (C) | 441.1542 (+0.4 mDa) | 2.41 | 4 |
| 28 | 143.09 (C) | 427.1381 (−0.1 mDa) | 1.99 | 4 |
| 29 | 212.99 (C) | 442.1495 (+0.4 mDa) | 1.89 | 4 |
| 30 | 159.31 (C) | 442.1494 (+0.3 mDa) | 1.92 | 4 |
| 31 | 147.39 (C) (*) | 461.1105 (+0.1 mDa) | 2.46 | 4 |
| 32 | 170.35 (C) | 457.1599 (−0.1 mDa) | 2.70 | 4 |
| 33 | 188.85 (C) | 443.1451 (+0.8 mDa) | 2.42 | 4 |
| 34 | 136.57 (C) | 478.0851 (+0.3 mDa) | 3.03 | 7 |
| 35 | 173.63 (C) | 478.0848 (+0.0 mDa) | 3.04 | 7 | n.d. means not determined.
(*) Multiple crystalline forms detected. MP related to the main/highest peak Optical Rotations Optical rotations were measured on a Perkin-Elmer 341 polarimeter with a sodium lamp and reported as follows: [α]° (λ, c g/100 ml, solvent, T ° C.). $[\alpha]_\lambda^T = (100\alpha)/(l \times c)$: where l is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 mL).

TABLE 4

Optical Rotation data.

| Co. No. | $\alpha_D$ (°) | Wavelength (nm) | Concentration w/v % | Solvent | Temp. (° C.) |
|---|---|---|---|---|---|
| 1 | +12.9 | 589 | 0.49 | DMF | 20 |
| 2 | +15.0 | 589 | 0.51 | DMF | 20 |
| 3 | +12.1 | 589 | 0.47 | DMF | 20 |
| 4 | +26.4 | 589 | 0.45 | DMF | 20 |
| 6 | +14.0 | 589 | 0.47 | DMF | 20 |
| 7 | +15.2 | 589 | 0.47 | DMF | 20 |
| 8 | +13.4 | 589 | 0.51 | DMF | 20 |
| 9 | +13.4 | 589 | 0.45 | DMF | 20 |
| 10 | +13.3 | 589 | 0.47 | DMF | 20 |
| 11 | +15.2 | 589 | 0.4 | DMF | 20 |
| 12 | +12.6 | 589 | 0.5 | DMF | 20 |
| 13 | +12.3 | 589 | 0.84 | DMF | 20 |
| 15 | +12.7 | 589 | 0.58 | DMF | 20 |
| 17 | +5.8 | 589 | 0.59 | DMF | 20 |
| 18 | +7.8 | 589 | 0.53 | DMF | 20 |
| 19 | +17.0 | 589 | 0.50 | DMF | 20 |
| 20 | +12.8 | 589 | 0.58 | DMF | 20 |
| 21 | +11.5 | 589 | 0.56 | DMF | 20 |
| 22 | +13.6 | 589 | 0.50 | DMF | 20 |
| 23 | +85.6 | 589 | 0.54 | DMF | 20 |
| 24 | −6.6 | 589 | 0.49 | DMF | 20 |
| 25 | +7.9 | 589 | 0.64 | DMF | 20 |
| 26 | 12.1 | 589 | 0.54 | DMF | 20 |
| 28 | −3.0 | 589 | 0.55 | DMF | 20 |
| 29 | −5.5 | 589 | 0.53 | DMF | 20 |
| 30 | +9.9 | 589 | 0.54 | DMF | 20 |
| 31 | +3.4 | 589 | 0.59 | DMF | 20 |
| 32 | −15.9 | 589 | 0.54 | DMF | 20 |
| 33 | −15.2 | 589 | 0.53 | DMF | 20 |
| 34 | +221.2 | 589 | 0.51 | DMF | 20 |
| 35 | +8.3 | 589 | 0.50 | DMF | 20 |

Pharmacological Examples

A) In Vitro Pharmacology

The compounds provided in the present invention are negative allosteric modulators of mGluR2. These compounds appear to inhibit glutamate responses by binding to an allosteric site other than the glutamate binding site. The response of mGluR2 to a concentration of glutamate is decreased when compounds of Formula (I) are present. Compounds of Formula (I) are expected to have their effect substantially at mGluR2 by virtue of their ability to reduce the function of the receptor. The effects of negative allosteric modulators tested at mGluR2 using the [$^{35}$S]GTPγS binding assay method described below and which is suitable for the identification of such compounds, and more particularly the compounds according to Formula (I), are shown in Table 5.

1) [$^{35}$S]GTPγS Binding Assay

The [$^{35}$S]GTPγS binding assay is a functional membrane-based assay used to study G-protein coupled receptor (GPCR) function whereby incorporation of a non-hydrolysable form of GTP, [$^{35}$S]GTPγS (guanosine 5'-triphosphate, labelled with gamma-emitting $^{35}$S), is measured. The G-protein α subunit catalyzes the exchange of guanosine 5'-diphosphate (GDP) by guanosine triphosphate (GTP) and on activation of the GPCR by an agonist, [$^{35}$S]GTPγS, becomes incorporated and cannot be cleaved to continue the exchange cycle (Harper (1998) Current Protocols in Pharmacology 2.6.1-10, John Wiley & Sons, Inc.). The amount of radioactive [$^{35}$S]GTPγS incorporation is a direct measure of the activity of the G-protein and hence the activity of the antagonist can be determined. mGlu2 receptors are shown to be preferentially coupled to Gαi-protein, a preferential coupling for this method, and hence it is widely used to study receptor activation of mGlu2 receptors both in recombinant cell lines and in tissues. Here we describe the use of the [$^{35}$S]GTPγS binding assay using membranes from cells transfected with the human mGlu2 receptor and adapted from Schaffhauser et al. (Molecular Pharmacology, 2003, 4:798-810) for the detection of the negative allosteric modulation (NAM) properties of the compounds of this invention.

Membrane Preparation

CHO-cells were cultured to pre-confluence and stimulated with 5 mM butyrate for 24 h. Cells were then collected by scraping in PBS and cell suspension was centrifuged (10 min at 4000 RPM in benchtop centrifuge). Supernatant was discarded and pellet gently resuspended in 50 mM Tris-HCl, pH 7.4 by mixing with an Ultra Turrax homogenizer. The suspension was centrifuged at 12,400 RPM (Sorvall F14S-6x250Y) for 10 minutes and the supernatant discarded. The pellet was homogenized in 5 mM Tris-HCl, pH 7.4 using an Ultra Turrax homogenizer and centrifuged again (13,000 RPM, 20 min, 4° C.). The final pellet was resuspended in 50 mM Tris-HCl, pH 7.4 and stored at −80° C. in appropriate aliquots before use. Protein concentration was determined by the Bradford method (Bio-Rad, USA) with bovine serum albumin as standard.

[$^{35}$S]GTPγS Binding Assay

Measurement of mGluR2 negative allosteric modulatory activity of test compounds was performed as follows. Test compounds and glutamate were diluted in assay buffer containing 10 mM HEPES acid, 10 mM HEPES salt, pH 7.4, 100 mM NaCl, 3 mM MgCl$_2$ and 10 μM GDP. Human mGlu2 receptor-containing membranes were thawed on ice and diluted in assay buffer supplemented with 18 μg/ml saponin. Membranes were pre-incubated with compound together with a predefined (~EC$_{80}$) concentration of glutamate (60 μM) for 30 min at 30° C. After addition of [$^{35}$S]GTPγS (f.c. 0.1 nM), assay mixtures were shaken briefly and further incubated to allow [$^{35}$S]GTPγS incorporation on activation (30 minutes, 30° C.). Final assay mixtures contained 7 μg of membrane protein in 10 mM HEPES acid, 10 mM HEPES salt, pH 7.4, 100 mM NaCl, 3 mM MgCl$_2$, 10 μM GDP and 10 μg/ml saponin. Total reaction volume was 200 μl. Reactions were terminated by rapid filtration through Unifilter-96 GF/B plates (Perkin Elmer, Massachusetts, USA) using a 96-well filtermate universal harvester. Filters were washed 6 times with ice-cold 10 mM NaH$_2$PO$_4$/10 mM Na$_2$HPO$_4$, pH 7.4. Filters were then air-dried and 30 μl of liquid scintillation cocktail (Microscint-O) was added to each well. Membrane-bound radioactivity was counted in a Topcount.

Data Analysis

The concentration-response curves of representative compounds of the present invention were generated using the Lexis software interface (developed at J&J). Data were calculated as % of the control glutamate response, defined as the response that is generated upon addition of an EC$_{80}$-equivalent concentration of glutamate. Sigmoid concentration-response curves plotting these percentages versus the log concentration of the test compound were analyzed using non-linear regression analysis. The concentration producing half-maximal inhibition was calculated as the IC$_{50}$. The pIC$_{50}$ values were calculated as the −log IC$_{50}$, when the IC$_{50}$ is expressed in M. E$_{max}$ is defined as the relative maximal effect (i.e. maximal % inhibition relative to the control glutamate response).

TABLE 5

Pharmacological data for compounds according to the invention.

| Co. No. | GTPγS - hmGluR2 anGT pIC$_{50}$ | GTPγS - hmGluR2 anGT Emax |
|---|---|---|
| 1 | 8.8 | 106 |
| 8 | 8.07 | 107 |
| 2 | 8.95 | 105 |
| 4 | 8.62 | 103 |
| 5 | 8.39 | 105 |
| 9 | 8.06 | 107 |
| 11 | 7.99 | 103 |
| 10 | 8 | 105 |
| 6 | 8.25 | 106 |
| 3 | 8.65 | 105 |
| 7 | 8.17 | 105 |
| 12 | 7.48 | 107 |
| 13 | 8.96 | 108 |
| 16 | 8.15 | 104 |
| 17 | 7.83 | 105 |
| 18 | 8.57 | 107 |
| 19 | 8.67 | 104 |
| 20 | 7.62 | 102 |
| 21 | 7.38 | 102 |
| 22 | 9.08 | 106 |

TABLE 5-continued

Pharmacological data for compounds according to the invention.

| Co. No. | GTPγS - hmGluR2 anGT pIC$_{50}$ | GTPγS - hmGluR2 anGT Emax |
|---|---|---|
| 23 | 8.56 | 106 |
| 24 | 7.80 | 99 |
| 25 | 8.65 | 105 |
| 26 | 7.43 | 108 |
| 27 | 7.01 | 106 |
| 28 | 7.27 | 101 |
| 29 | 8.53 | 106 |
| 31 | 8.06 | 111 |
| 32 | 8.03 | 106 |
| 33 | 8.60 | 109 |
| 34 | 7.84 | 110 |
| 35 | 7.37 | 108 |

B) In Vivo Pharmacology

1) Reversal of LY-404039-Induced Decrease of Palpebral Opening in Apomorphine-Challenged Rats.

Male Wiga Wistar rats (Crl:WI; Charles River Germany; 220±40 g) were housed under standard laboratory conditions (21±2° C.; 50-65% relative humidity; light-dark cycle set at 12 h; lights on at 6.00 h) and fasted overnight prior to the start of the experiments (tap water remained available ad libitum). During the test period, they were housed in individual cages. Palpebral opening was scored every 5 min over the first hour after injection of apomorphine (1.0 mg/kg, i.v.) in animals either pretreated or not pretreated with LY-404039 (2.5 mg/kg, s.c.) at 1 h prior to the apomorphine injection. The animals were also pretreated with test compound or solvent at a predefined interval before apomorphine challenge. The score system was: (5) exophthalmos, (4) wide open, (3) open for three-quarters, (2) half open, (1) open for one-quarter, (0) closed. The scores for palpebral opening were cumulated over the 60-min observation period. A cumulative palpebral opening score >26 was selected for drug-induced reversal of the LY-404039-induced decrease of palpebral opening (occurrence in 3.2% of control animals pretreated with LY-404039 (n=154) versus in 99.5% of control rats not pretreated with LY-404039 (n=6335)).

Table 6 shows the palpebral opening score in control animals receiving apomorphine alone and in animals receiving apomorphine and LY-404039. In animals receiving apomorphine alone the median palpebral opening is 43 whereas in animals receiving apomorphine and LY-404039, the median palpebral opening is 17. In animals treated with apomorphine alone, the palpebral opening score is almost always (in 95.5% of the rats) greater than 34, whereas in animals treated with the combination (apomorphine+LY-404039) only 3.2% of the animals show a palpebral opening greater than 26.

TABLE 6

Palpebral opening score in control animals.

| Measurement | Apomorphine alone (n = 6335) | Apomorphine + LY-404039 (n = 154) |
|---|---|---|
| Palpebral opening score | | |
| Median score: | 43 | 17 |
| Occurrence score >26 (%): | 99.5 | 3.2 |
| Occurrence score >34 (%): | 95.9 | 0.0 |

2) Reversal of the Effect of the mGluR2 PAM JNJ-42153605-Induced Inhibition of Scopolamine-Induced Hyperlocomotion Apparatus Motor activity was measured in microprocessor-based motor activity arenas (closed gray PVC cylinders with a height of 39 cm and a diameter of 31 cm). Each arena was placed on an infrared LED (8×8 LEDs) lit box (white PVC squared box; 40×40 cm$^2$; height 12.5 cm. An infrared-sensitive tube camera and a white light source were mounted to the ceiling above the observation chamber to track the animal. The total distance traveled (cm) was recorded and analyzed using the Noldus Ethovision XT Video Tracking System (Version 7.0.418; Noldus, Wageningen, The Netherlands). The intensity of the light within the activity cages (measured in the centre at the level of the floor) ranged between 4 and 8 LUX.

General Procedure

The rats were pretreated with test compound or vehicle at 60 min before the start of the activity recordings and placed into individual cages. The rats were challenged with JNJ-42153605 (3-(cyclopropylmethyl)-7-(4-phenylpiperidin-1-yl)-8-(trifluoromethyl)-[1,2,4]triazolo[4,3-a]pyridine; WO2010/130424; Cid et al. *J. Med. Chem.* 2012, 55, 8770-8789) (20 mg/kg, i.v.) 30 min before the start of the activity recording combined with scopolamine (0.16 mg/kg, i.v.) just before the start of the activity measurements. Immediately after the injection of scopolamine, the rats were placed into the activity monitors and total distance travelled over the first 30 min was measured.

Solvent-Pretreated Control Rats.

Frequency distributions obtained in a historical series of solvent-pretreated control rats are given in Table 7 below. Animals receiving the combination of JNJ-42153605 and scopolamine (n=433) almost always travelled a distance of less than 1500 cm (<1500 cm) (only 2.5% of the control rats travelled a distance of more than 1500 cm (>1500 cm)). On the other hand, animals challenged with scopolamine alone (n=215) always travelled a total distance of more than 1500 cm (>1500 cm) and almost always (in 95.8% of the rats) a distance of more than 4400 cm (>4400 cm). Rats that did not receive any challenge travelled almost always a distance of more than 1500 cm (>1500 cm) (in 93.3% of the rats) and less than 4400 cm (<4400 cm) (in 98.9% of the rats). For reversal of the inhibitory effect of JNJ-42153605 on the scopolamine-induced hyperlocomotion, the following all-or-none criteria were adopted: (1) reversal: total distance >1500 cm.

TABLE 7

Frequency distributions obtained in historical series of solvent-pretreated control rats.

| | Median (cm) | >1500 cm (%) | >4400 cm (%) | $N_{tested}$ |
|---|---|---|---|---|
| Combination | 480 | 2.5 | 0.0 | 433 |
| No challenge | 2618 | 93.3 | 1.1 | 638 |
| Scopolamine | 7246 | 100 | 95.8 | 215 |

$N_{tested}$ means number of animals tested.

3) Induction of Mydriasis

The pupil diameter of Wiga rats was measured with a microscopic micrometer (1 unit=1/24 mm). Criteria for drug-induced effects: pupil diameter >25 units for mydriasis (in controls: 1.9%) 1 h post-administration of the test compound (test 1) or 1, 2 or 3 h post-administration of the test compound (test 2, wherein the maximum pupil diameter over the full 3 h period is reported).

Table 8 below provides the data obtained in the tests 1)-3) described above:

TABLE 8

Summary of data in tests 1)-3).

| | | $ED_{50}$ (mg/kg) | | | |
|---|---|---|---|---|---|
| Co. | | SCOP JNJ- | APO | MYD | |
| No. | Route | 42153605 | LY-404039 | Test 1 | Test 2 |
| 1 | PO | 0.17 | 0.08 | >10 | >40 |
| | SC | | 0.06 | | |
| 13 | PO | 0.028 | | | >40 |
| 22 | | >0.63 | | | |
| 25 | | 0.08 | | | |
| 18 | | 0.13 | | | |
| 19 | | >0.63 | | | |
| 29 | | >0.63 | | | |

In the table:
SCOP JNJ-42153605 means Reversal of the effect of JNJ 42153605 on scopolamine-induced hyperlocomotion,
APO LY-404039 means Reversal of LY-404039-induced decrease of palpebral opening in apomorphine challenged rats,
MYD means Induction of mydriasis,
$ED_{50}$ means median effective dose;
PO means oral route;
SC means subcutaneous route.

Prophetic Composition Examples

"Active ingredient" as used throughout these examples relates to a final compound of Formula (I), the pharmaceutically acceptable salts thereof, the solvates and the stereochemically isomeric forms and the tautomers thereof.

Typical examples of recipes for the formulation of the invention are as follows:

| 1. Tablets | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

| 4. Ointment | |
|---|---|
| Active ingredient | 5 to 1000 mg |
| Stearyl alcohol | 3 g |

| 4. Ointment | |
|---|---|
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

We claim:

1. A compound of Formula (I)

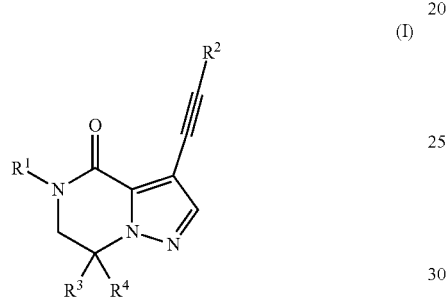

or a stereoisomeric form thereof, wherein
$R^1$ is phenyl or 2-pyridinyl, each of which is optionally substituted with one or more substituents each independently selected from the group consisting of halo, $C_{1-4}$alkyl, monohalo-$C_{1-4}$alkyl, polyhalo-$C_{1-4}$alkyl, —$C_{1-4}$alkyl-OH, —CN, —$C_{1-4}$alkyl-O—$C_{1-4}$alkyl, $C_{3-7}$cycloalkyl, —O—$C_{1-4}$alkyl, monohalo-$C_{1-4}$alkyloxy, polyhalo-$C_{1-4}$alkyloxy, $SF_5$, $C_{1-4}$alkylthio, monohalo-$C_{1-4}$alkylthio and polyhalo-$C_{1-4}$alkylthio;
$R^2$ is phenyl or pyridinyl, each of which is optionally substituted with one or more substituents each independently selected from the group consisting of halo, $C_{1-4}$alkyl, monohalo-$C_{1-4}$alkyl, polyhalo-$C_{1-4}$alkyl, —OH, —O—$C_{1-4}$alkyl, —$C_{1-4}$alkyl-O—$C_{1-4}$alkyl, monohalo-$C_{1-4}$alkyloxy, polyhalo-$C_{1-4}$alkyloxy, —$C_{1-4}$ alkyl-OH and $NR^{5a}R^{5b}$;
wherein $R^{5a}$ and $R^{5b}$ are each independently selected from the group consisting of hydrogen or $C_{1-4}$alkyl;
$R^3$ is selected from the group consisting of hydrogen or $C_{1-4}$alkyl;
$R^4$ is selected from the group consisting of hydrogen, $C_{1-4}$alkyl, monohalo-$C_{1-4}$alkyl, polyhalo-$C_{1-4}$alkyl, —$C_{1-4}$alkyl-O—$C_{1-4}$alkyl and —$C_{1-4}$alkyl-OH;
or a N-oxide, or a pharmaceutically acceptable salt thereof.

2. The compound according to claim 1, wherein
$R^1$ is phenyl or 2-pyridinyl, each optionally substituted with one or two substituents each independently selected from the group consisting of halo, $C_{1-4}$alkyl, monohalo-$C_{1-4}$alkyl, polyhalo-$C_{1-4}$alkyl, —$C_{1-4}$alkyl-O—$C_{1-4}$alkyl, and monohalo-$C_{1-4}$alkyloxy, polyhalo-$C_{1-4}$alkyloxy;
$R^2$ is phenyl or pyridinyl, each of which is optionally substituted with one or two substituents each independently selected from the group consisting of halo, $C_{1-4}$alkyl, monohalo-$C_{1-4}$alkyl, polyhalo-$C_{1-4}$alkyl, —O—$C_{1-4}$alkyl, —$C_{1-4}$alkyl-O—$C_{1-4}$alkyl, monohalo-$C_{1-4}$alkyloxy, polyhalo-$C_{1-4}$alkyloxy, and $NR^{5a}R^{5b}$;
wherein $R^{5a}$ and $R^{5b}$ are each independently selected from the group consisting of hydrogen or $C_{1-4}$alkyl;
$R^3$ is hydrogen;
$R^4$ is selected from the group consisting of $C_{1-4}$alkyl or —$C_{1-4}$alkyl-O—$C_{1-4}$alkyl;
or a N-oxide, or a pharmaceutically acceptable salt thereof.

3. The compound according to claim 1 wherein
$R^1$ is phenyl or 2-pyridinyl, each optionally substituted with one or two substituents each independently selected from the group consisting of halo, polyhalo-$C_{1-4}$alkyl, and —O—$C_{1-4}$alkyl;
$R^2$ is phenyl or pyridinyl, each of which is optionally substituted with one or two substituents each independently selected from the group consisting of halo, $C_{1-4}$alkyl, —O—$C_{1-4}$alkyl, and $NR^{5a}R^{5b}$;
wherein $R^{5a}$ and $R^{5b}$ are each independently selected from the group consisting of hydrogen or $C_{1-4}$alkyl;
$R^3$ is hydrogen;
$R^4$ is $C_{1-4}$alkyl;
or a N-oxide, or a pharmaceutically acceptable salt thereof.

4. The compound according to claim 1, wherein $R^3$ is hydrogen and $R^4$ is a substituent different from hydrogen having a configuration as depicted in the Formula (I')

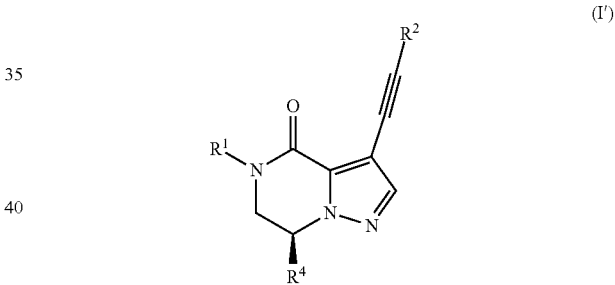

wherein the 6,7-dihydropyrazolo[1,5-a]pyrazin-4(5H)-one core, $R^1$ and $R^2$ are in the plane of the drawing and $R^4$ is projected above the plane of the drawing.

5. A pharmaceutical composition comprising a therapeutically effective amount of a compound as defined in claim 1 and a pharmaceutically acceptable carrier or excipient.

6. A process for preparing the pharmaceutical composition comprising intimately mixing a pharmaceutically acceptable carrier with a therapeutically effective amount of a compound as defined in claim 1.

7. A method of treating a central nervous system disorder or condition selected from the group consisting of mood disorders; delirium; dementia; amnestic disorders; substance-related disorders; psychotic disorders; somatoform disorders; and hypersomnic sleep disorder, comprising administering to a subject in need thereof, a therapeutically effective amount of a compound as defined in claim 1.

8. A method of treating a central nervous system disorder or condition selected from the group consisting of depressive disorders; neurocognitive disorders; neurodevelopmental disorders; substance-related and addictive disorders; schizophrenia spectrum; somatic symptom disorders; and hypersomnolence disorder; comprising administering to a subject in need thereof, a therapeutically effective amount of a compound as defined in claim 1.

9. The method according to claim 8 wherein the depressive disorder is selected from the group consisting of major depressive disorder and treatment resistant depression.

10. The method of claim 7 wherein an effective amount of an additional pharmaceutical agent is administered simultaneously or sequentially in the treatment of central nervous system conditions.

11. The method of claim 8 wherein an effective amount of an additional pharmaceutical agent is administered simultaneously or sequentially.

12. The compound according to claim 1, wherein the compound is or a pharmaceutically acceptable salt thereof.

13. The compound according to claim 1, wherein the compound is or a pharmaceutically acceptable salt thereof.

14. The compound according to claim 1, wherein the compound is

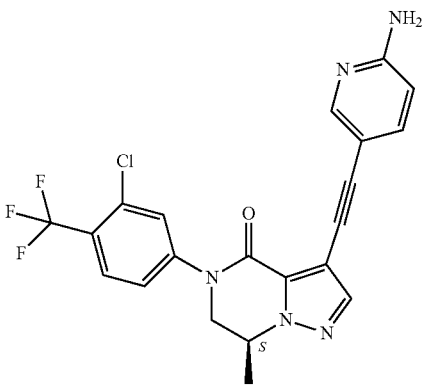

or a pharmaceutically acceptable salt thereof.

15. A method of treating a depressive disorder comprising administering to a patient in need thereof a therapeutically effective amount of a compound according to claim 12.

16. The method of claim 15 wherein the depressive disorder is selected from the group consisting of major depressive disorder and treatment resistant depression.

17. A method of treating a depressive disorder comprising administering to a patient in need thereof a therapeutically effective amount of a compound according to claim 13.

18. The method of claim 17 wherein the depressive disorder is selected from the group consisting of major depressive disorder and treatment resistant depression.

19. A method of treating a depressive disorder comprising administering to a patient in need thereof a therapeutically effective amount of a compound according to claim 14.

20. The method of claim 19 wherein the depressive disorder is selected from the group consisting of major depressive disorder and treatment resistant depression.

21. The method of claim 10 wherein an effective amount of an additional pharmaceutical agent is administered simultaneously or sequentially.

22. The method of claim 15 wherein an effective amount of an additional pharmaceutical agent is administered simultaneously or sequentially.

23. The method of claim 17 wherein an effective amount of an additional pharmaceutical agent is administered simultaneously or sequentially.

24. The method of claim 19 wherein an effective amount of an additional pharmaceutical agent is administered simultaneously or sequentially.

* * * * *